(12) United States Patent
Devroye

(10) Patent No.: US 11,957,375 B2
(45) Date of Patent: Apr. 16, 2024

(54) SYSTEM, APPARATUS, AND METHOD FOR FOLLICULAR UNIT EXTRACTION

(71) Applicant: Devroye Instruments Belgium, Etterbeek (BE)

(72) Inventor: Jean Devroye, Brussels (BE)

(73) Assignee: DEVROYE INSTRUMENTS BELGIUM, Etterbeek (BE)

( * ) Notice: Subject to any disclaimer, the term of this patent is extended or adjusted under 35 U.S.C. 154(b) by 624 days.

(21) Appl. No.: 17/251,545

(22) PCT Filed: Jun. 11, 2019

(86) PCT No.: PCT/US2019/036552
§ 371 (c)(1),
(2) Date: Dec. 11, 2020

(87) PCT Pub. No.: WO2019/241247
PCT Pub. Date: Dec. 19, 2019

(65) Prior Publication Data
US 2021/0251649 A1    Aug. 19, 2021

Related U.S. Application Data

(60) Provisional application No. 62/683,274, filed on Jun. 11, 2018.

(51) Int. Cl.
*A61B 17/3205* (2006.01)
*A61B 17/00* (2006.01)

(52) U.S. Cl.
CPC ............ *A61B 17/32053* (2013.01); *A61B 2017/00221* (2013.01); *A61B 2017/00398* (2013.01);
(Continued)

(58) Field of Classification Search
CPC .... A61B 17/32053; A61B 2017/00398; A61B 2017/00473; A61B 2017/00752; A61B 2217/005
See application file for complete search history.

(56) References Cited

U.S. PATENT DOCUMENTS 8,211,117 B2    7/2012  Harris
2007/0106306 A1*  5/2007  Bodduluri ............ A61B 34/70
                                                   606/133

(Continued)

FOREIGN PATENT DOCUMENTS

EP       2519170 B1    11/2012
KR    101993315 B1     6/2019
(Continued)

OTHER PUBLICATIONS

International Search Report and Written Opinion issued in corresponding International Appl. No.: PCT/US19/36552 dated Oct. 31, 2019 (10 pages).

*Primary Examiner* — Sarah A Long
(74) *Attorney, Agent, or Firm* — Carter, DeLuca & Farrell, LLP; David C. Lee, Esq.

(57) ABSTRACT

Disclosed herein is a system, method, and apparatus for harvesting follicular units from an epidermis. The disclosed apparatus includes a hollow tubular structure having a central axis and an end structure that is attached to an end of the hollow tubular structure. The end structure terminates distally at a substantially flat annular face that is substantially in a plane perpendicular to the central axis. The flat annular face has a sharp outer edge.

20 Claims, 24 Drawing Sheets

(52) U.S. Cl.
CPC .............. *A61B 2017/00473* (2013.01); *A61B 2017/00752* (2013.01); *A61B 2017/00973* (2013.01); *A61B 2217/005* (2013.01)

(56) References Cited

U.S. PATENT DOCUMENTS

| | | | |
|---|---|---|---|
| 2009/0240261 A1* | 9/2009 | Drews | ................... A61B 34/10 606/133 |
| 2010/0082041 A1 | 4/2010 | Prisco | |
| 2010/0082042 A1 | 4/2010 | Drews | |
| 2014/0171827 A1 | 6/2014 | Westerling, Jr. et al. | |
| 2016/0015963 A1* | 1/2016 | Grace | ............ A61B 17/320016 606/129 |

FOREIGN PATENT DOCUMENTS

| | | |
|---|---|---|
| WO | 2008115526 A2 | 9/2008 |
| WO | 2018009232 A1 | 1/2018 |

\* cited by examiner

SYSTEM, APPARATUS, AND METHOD FOR FOLLICULAR UNIT EXTRACTION

CROSS-REFERENCE TO RELATED APPLICATIONS

The present application is a National Stage of, and claims priority to and the benefit of, International Patent Application No. PCT/US2019/036552 filed Jun. 11, 2019, which, in turn, claims the benefit of and priority to U.S. Provisional Application No. 62/683,274, filed Jun. 11, 2018, which is hereby incorporated by reference herein in its entirety.

FIELD OF THE INVENTION

The disclosed technology relates to systems, apparatus, and methods for harvesting all or part of hair follicles, commonly referred to as follicular units.

BACKGROUND

During the past eighteen years, an original technique for harvesting hair grafts for performing hair grafts was developed by Dr. R. Woods, Dr. R. Bernstein and Dr. W. Rassman as well as many pioneers which include Dr. J. Cole, Dr. Jones, Dr. P. Rose, Dr. J. Harris, etc. This technique consists of using a sharp micro-tube, driven down around a small grouping of hairs called follicles. The maneuver is what is commonly called a scoring and is known as "FUE" which stands for Follicular Unit Extraction or Follicular unit excision.

The skin is composed of two distinct parts—firstly the epidermis, which is superficial and elastic but strong and very difficult to penetrate without the help of a sharp instrument, and secondly a dermal part, which is deeper and looser and more easily dissected using a blunt instrument.

The technique using sharp extraction instruments (referred to as "sharp punches") is typically a two-step technique. Step 1 consists of rotating the punch around the hairs composing the follicle. Step 2: When the follicle is partially detached from the surrounding tissue, it is possible to extract it by grasping it by its tip. This maneuver corresponds to the actual follicular extraction.

The first method chosen by the majority of practitioners is to use sharp, even ultra sharp punches. The reasoning is as follows: the sharper the punch, the less it will deform the follicle within the skin during step 1 of the follicular extraction, and by decreasing the deformation of the follicular unit they hope to decrease the rate of transection.

The majority of the punches commercially available at present are thus sharp or very sharp. There are many examples of these punches including the following references:

Restoration Robotics
U.S. Pat. No. 8,211,116 B2
Dr. John Cole
US 20070156164 A1
U.S. Pat. No. 9,204,892 B2
WO 2007/087463 A2
Dr. Sanusi Umar
US 20110160746 A1

They have the particularity of ending with a tapered triangular end, which is very aggressive. The sharp part is always directed in the same axis as the central axis of the tube, which is also the axis along which the punch moves, as shown in, for example, FIG. 2 illustrating punches according to Cole and Artas.

The practitioner, however, faces a major insoluble problem with sharp punches. Indeed, the follicles almost always have the following characteristic: they are arranged in the shape of a cone. The upper end of the cone corresponds to the output of the hair at skin level while its lower base corresponds to the follicular zone of these hairs, as shown in FIG. 1.

On the other hand, the follicle is firmly attached to surrounding structures. To be able to detach a follicle in order to extract it without damage (Step 2), the punch must be pushed in deep enough; that is to say about 3-4 mm below the epidermis. Given the conical shape of the follicle, the result of using sharp punches is often transection—that is to say, the full section of one or more of the hairs is cut (transected) and remains captive in the donor zone. This has the effect of reducing the number of transferred hairs and thereby reducing the quality of the surgical intervention.

The orientation of the sharp punch is also crucial. Indeed, the slightest deviation from the axis of movement causes contact between the cutting portion and the hair, which causes at best a superficial abrasion, called paring, and at worst a full section of hair remaining in the donor zone, called a transection.

Consequently, it is often necessary to reduce the depth of the incision made with a sharp punch, such as limiting the incision depth to 2 mm below the epidermis, and/or to increase the diameter of the punch to obtain grafts with a low transection rate. This has the effect of increasing the size of scars and of damaging the follicles adjacent to the one being extracted. Furthermore, when a sharp punch only slightly penetrates the dermis, the extraction process (Step 2) is slowed with a risk of damaging the follicles during extraction. So this lengthens the overall duration of the intervention.

Numerous specific systems to limit the depth of insertion of sharp punches have been proposed. For example, Dr. John Cole has developed such systems on his follicular extraction instruments.

Even so, it is common to find that despite the efforts of practitioners, the rate of removed follicles that are damaged or completely cut is often significant and sometimes enormous. It is not uncommon, using sharp punches, to find harvests with more than 20 to 40% of damaged hairs or follicles.

The second method developed about 15 years ago has been to subdivide Step 1 into two steps with the use of two different punches. This second method was named the "3 step" technique. The first step is the very superficial cutting of the epidermis with the aid of a sharp punch. The second step is to then use a blunt or dull punch to dissect the dermal tissue around the hairs without damaging them. And the third step is the actual extraction. The technique dates from 2004 and was invented by Dr. James Harris. FIG. 3 illustrates an example of Dr. Harris' instrument.

This same principle was adopted by the Restoration Robotics Company, which still currently uses a system consisting of two punches on its Artas robot—one sharp punch is enclosed in a blunt punch that slides around it, as shown in FIG. 4. The two punches work successively.

There are disadvantages to the two-step technique and the 3-step technique. Accordingly, there is continued interest in development of improved follicular extraction instruments.

SUMMARY

The present invention relates to a device and a method for harvesting all or part of follicles commonly called follicular units. The disclosed device includes a hollow tube-like punching tool suitable for producing cores in the scalp. With respect to the disclosed tool, the term "distal" refers to the end for contacting a skin donor site, and the term "proximal" refers to the end away from the skin donor site. The terms "internal" and "inner" refer to a portion closer to a central axis of the punch tool, and the terms "external" and "outer" refer to a portion farther away from the central axis of the punch tool. In various embodiments, the tool terminates distally at a flat end substantially perpendicular to the tube central axis, with the flat end having a non-cutting internal edge and an external sharp cutting edge. The edge or edges referred to herein need not be straight or continuous. In various embodiments, the external sharp cutting edge can be continuous or non-continuous, and rounded or toothed.

This disclosed tubular tool is commonly called a punch and may be referred to herein as a "hybrid punch." In one aspect of the disclosed technology, the punch is driven by a dedicated system that includes a foot pedal and a motor. This pedal activates the motor, which is to coupled to the punch. This pedal produces oscillation or rotation of the motor and, therefore, movement of the punch. The pedal is not a simple on-off switch. Rather it triggers an oscillatory rotation whose speed is proportional to the pedal stroke.

In various embodiments, the tool can be housed in a handpiece or device used in the dental industry and can be capable of being sterilized. The disclosed technology can decrease the transection of follicles, i.e., the partial or complete cut of one or more hairs composing this follicle, and thus greatly improve the quality of the FUE hair transplant surgery and the number of harvested grafts. The number of missing grafts, that is to say, the number of grafts completely transected or buried in the skin, therefore, decreases dramatically.

In accordance with aspects of the present disclosure, an apparatus for harvesting hair follicles from a skin donor site includes a hollow tubular structure having a central axis, an annular ledge attached to an end of the hollow tubular structure and terminating distally at a substantially flat annular face that is substantially in a plane perpendicular to the central axis, and a follicle receiving chamber. The annular ledge includes a top surface extending outward from the hollow tubular structure, the flat annular face having a non-cutting inner edge, and a side surface connecting the top surface and the flat annular face and that is at least one of: parallel to the central axis or perpendicular to the flat annular face, where a sharp cutting edge is formed by the connection of the side surface with the flat annular face. The follicle receiving chamber extends proximally from the non-cutting inner edge of the substantially flat annular face.

In accordance with aspects of the present disclosure, an apparatus for harvesting hair follicles from a skin donor site by rotating or oscillating motion includes a hollow tubular structure having a central axis, an annular ledge attached to an end of the hollow tubular structure and terminating distally at a substantially flat annular face that is substantially in a plane perpendicular to the central axis, and a follicle receiving chamber. The annular ledge includes a top surface extending outward from the hollow tubular structure, the substantially flat annular face having a non-cutting inner edge, and a beveled side surface connecting the top surface and the substantially flat annular face, where a sharp cutting edge is formed by the connection of the beveled side surface with the flat annual face. The follicle receiving chamber extends proximally from the non-cutting inner edge of the substantially flat annular face.

In various embodiments, the top surface is substantially perpendicular to the hollow tubular structure. In various embodiments, a junction formed by the top surface of the annular ledge and an outer wall of the hollow tubular structure is an abrupt angle.

In various embodiments, the follicle receiving chamber is smoothly varying.

In various embodiments, the flat annular face includes notches such that the sharp cutting edge is non-continuous. In various embodiments, the annular ledge includes teeth between the notches.

In accordance with aspects of the present disclosure, an apparatus for harvesting hair follicles from a skin donor site by rotating or oscillating motion includes a hollow tubular structure having a central axis, a structural skirt attached to an end of the hollow tubular structure and terminating distally at a substantially flat annular face that is substantially in a plane perpendicular to the central axis, and a follicle receiving chamber. The structural skirt includes the flat annular face having a non-cutting inner edge, and an inclined surface connecting the tubular structure and the flat annular face, where a sharp cutting edge is formed by the connection of the inclined surface with the flat annual face. The follicle receiving chamber extending proximally from the non-cutting inner edge of the substantially flat annular face.

In various embodiments, a junction formed by the inclined surface of the structural skirt and an outer wall of the hollow tubular structure is an abrupt angle.

In various embodiments, the follicle receiving chamber is smoothly varying.

In various embodiments, the flat annular face includes notches such that the sharp cutting edge is non-continuous. In various embodiments, the structural skirt includes teeth between the notches.

Further details and aspects of exemplary embodiments of the present disclosure are described in more detail below with reference to the appended figures.

DETAILED DESCRIPTION

The disclosed technology relates to hair follicle harvesting system, method, and apparatus that greatly reduces the rate of transection and missing grafts, even when using smaller diameter punches, and that increases harvesting rate with little or no damage to follicles during the extraction step. The system includes various parts. In particular, a pedal activates a motor, which communicates therewith via a cable or wirelessly. A handpiece can be fitted to the motor, and the pedal triggers movement of a punch held in the handpiece via a chuck.

A tool according to the disclosed technology combines in a single punch two seemingly opposing characteristics: a punch portion sharp enough to penetrate the epidermis easily and at the same time ensuring that this punch is sufficiently gentle so as to reduce damage to the hairs when it plunges into the dermal portion of the skin.

In accordance with aspects of the disclosed technology, the disclosed tool positions an annular sharp cutting edge at the outer perimeter of an annular face at the distal end of the tool. In various embodiments, the annular face at the distal end of the tool is substantially in a plane perpendicular to the central axis of the punch. A tool according to various embodiments of the disclosed technology has a hollow tubular structure with a central axis and an end structure that can include various shapes, which will be described in more detail later herein. In various embodiments, the end structures terminate distally in a substantially flat and ring-like/annular face extending substantially in a plane perpendicular to the central axis. The substantially flat annular face has a sharp cutting edge located at the outer perimeter, which can be continuous and substantially circular, or can be non-circular and jagged or tooth-like. The term "substantially" is used herein to indicate that a shape, alignment, or other characteristic is intended to have a described property and either may have the exact property or may not have exactly the described property because of manufacturing limitations or defects, wear and tear, or other similar limitations or factors.

Figure 1:
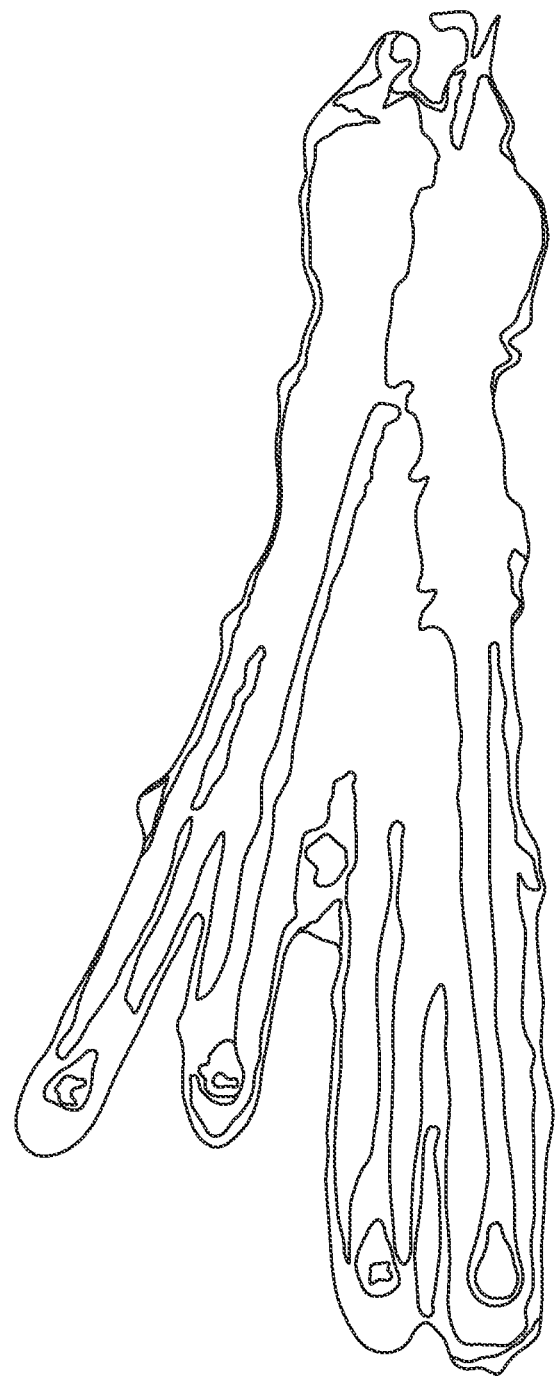
FIG. 1 schematically shows a follicle model with its classic conical shape.
Figure 2:
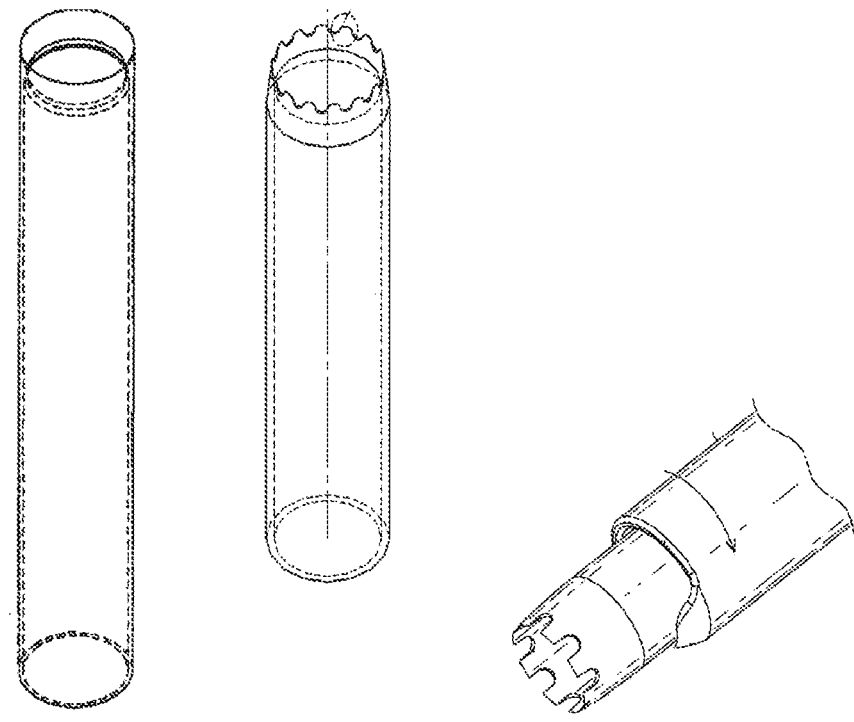
FIG. 2 shows examples of sharp punches according to Dr. John Cole and Artas.
Figure 3:
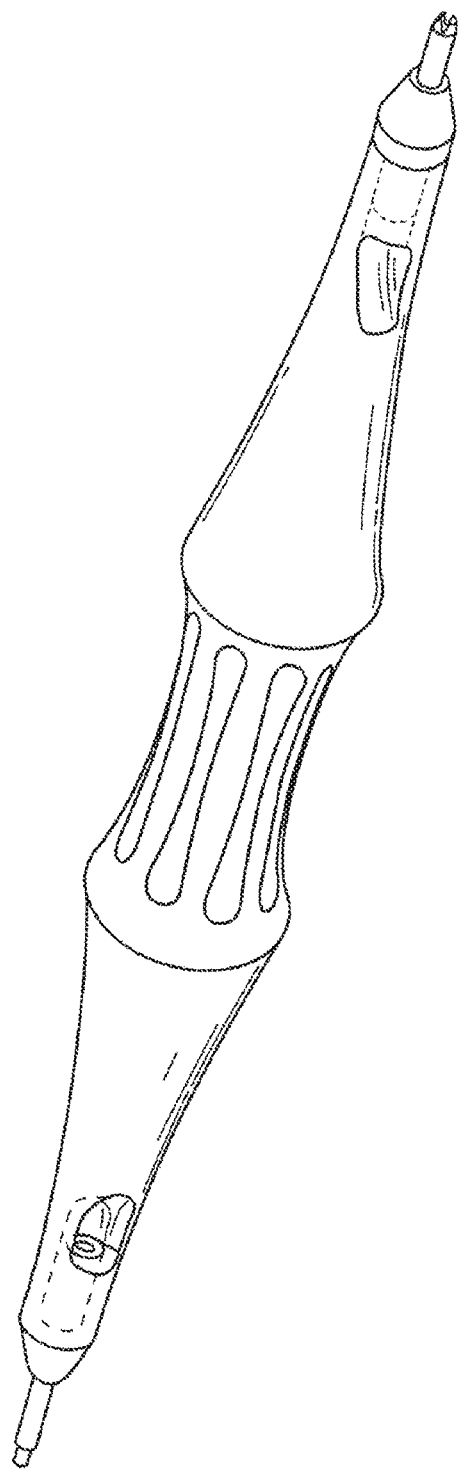
FIG. 3 shows an example of an extracting device according to Dr. James Harris comprising a handle, a sharp punch on one side of the handle, and a blunt punch on the other side of the handle.
Figure 4:
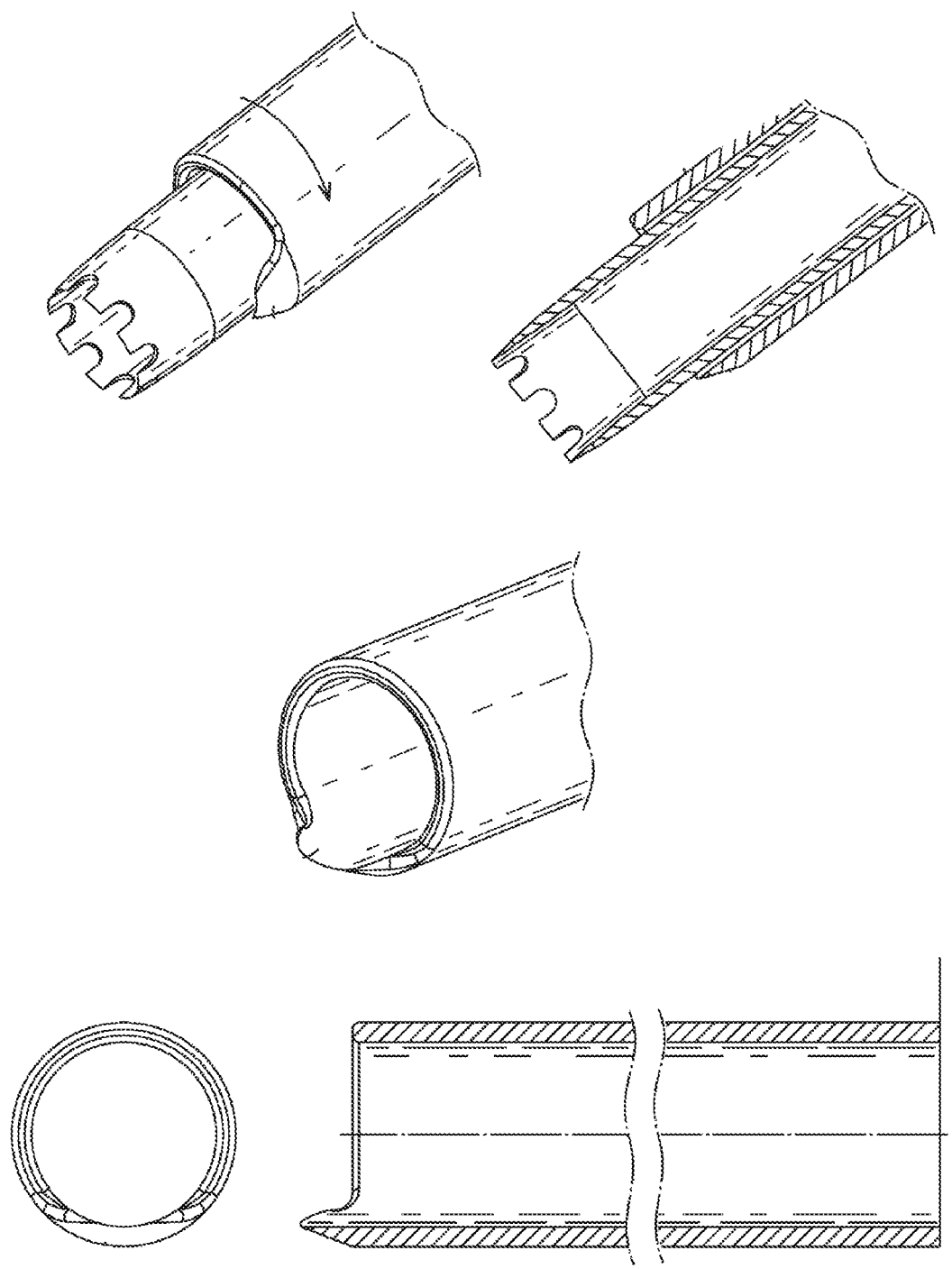
FIG. 4 shows an example of a tool from Restoration Robotics with two punches slidably mounted.
Figure 5:
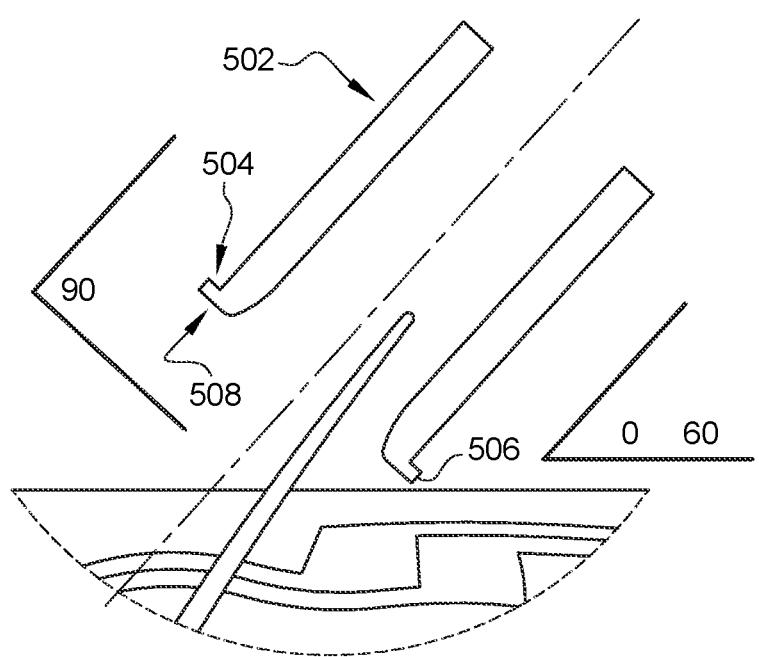
FIG. 5 shows an example of use of a tool according to the disclosed technology, during the epidermis-cutting step.

The operation of the tool according to the disclosed technology is shown in FIG. 5, which illustrates a cross-section of a hollow tubular structure 502 and an end structure 504 of one embodiment of the disclosed punch. The end structure 504 is shaped such that its interior appears as a funnel to the hair follicle. The cutting edge 506 is located on the outermost edge of the flat annular face 508 of the end structure and is located in a plane that is perpendicular to the central axis A of the hollow tubular structure 502. The funnel interior forms a portion of a follicle receiving chamber that extends proximally from a non-cutting inner edge of the flat annular face.

If this end structure is placed perpendicularly to the epidermis, the flat face 508 of the tool is supported on the skin in such a way that the rotation/oscillation of the tool relative to its central axis will not cut the epidermis when very little pressure is applied. On the other hand, if one pivots the tool so that its end portion is positioned in a plane at an angle of 30 to 60° with respect to the plane of the epidermis, the sharp cutting edge 506 is in contact with the epidermis and is capable of marking and cutting the skin during a rotary movement of the tool about its central axis.

Figure 6:
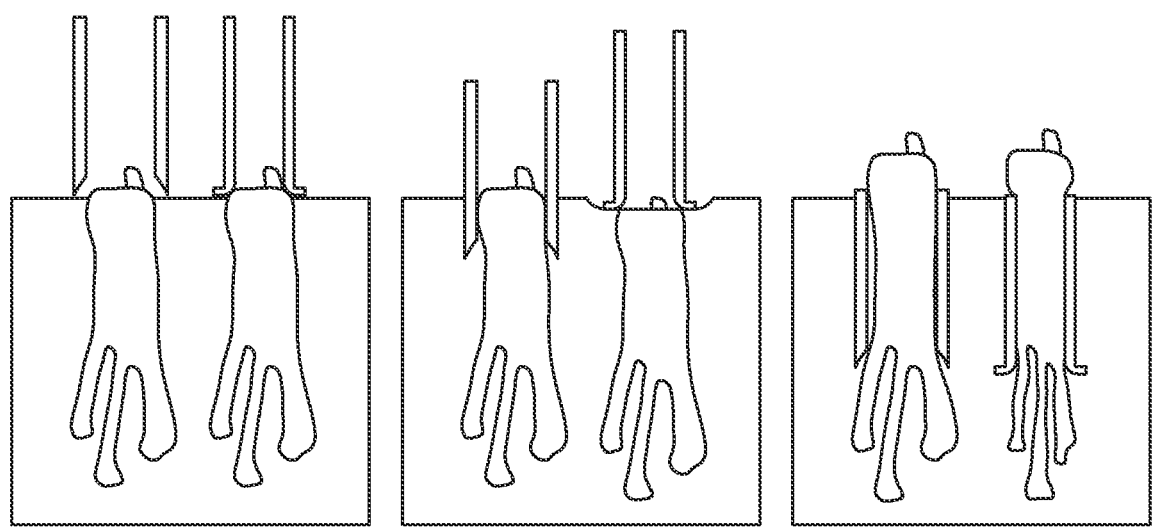
FIG. 6 shows an example of a follicle extraction process, in accordance with aspects of the disclosed technology.

In various embodiments, a punch according to the disclosed technology is positioned such that the skin is not approached perpendicularly but obliquely. The sharp cutting edge 506 of the end of the punch can therefore easily cut into the epidermis, which, as previously described, can be resistant. Once this barrier is passed, the movement of the punch can be controlled in order to move it parallel to the axis of the hairs, and therefore the cutting edge 506 also moves in such a way that it is remote from the hair to be harvested and therefore cannot damage the hairs/grafts that are harvested. In addition, these hairs are directed towards the center of the punch, as in a funnel, and touch the round inner portion of the punch, as shown in FIG. 5, which greatly reduces, or even eliminates, their transection and also reduces the damage that sharp punches usually cause. The funnel interior forms a portion of a follicle receiving chamber that extends proximally from an inner edge of the flat annular face. The follicle receiving chamber is not connected to the sharp cutting edge 506, and thus, hair follicles in the follicle receiving chamber will not be transected by the sharp cutting edge 506. In various embodiments, as shown in FIG. 6, the punch can approach the epidermis perpendicularly rather than obliquely, such that the flat annular face 508 contacts the skin, and a sufficient pressure of the punch placed perpendicularly to the skin can cut into the epidermis and provide the same result, as shown in FIG. 6.

Because the disclosed punch has both sharp and unsharp characteristics, they are referred to herein as "hybrid punches." Because the inside of the punch is smooth and/or not aggressive, it is possible to reduce the size of the punch used, and thus to reduce the injuries/scars around the hairs.

In one aspect of the disclosed technology, movement of the punch is a slow movement between approximately 60 and 300 revolutions per minute. In various embodiments, the movement is an oscillating movement such that rotation successively changes direction after having travelled a 30 to 360 degree course. The pedal which is included in the disclosed system (discussed below herein) allows one to change the speed of this movement with more or less pressure on the foot pedal.

The disclosed punch operates to harvest intact human follicular units during a hair transplant surgery. The disclosed harvesting tool has some of the beneficial characteristics of conventional sharp punches without being a sharp punch.

Figure 7:
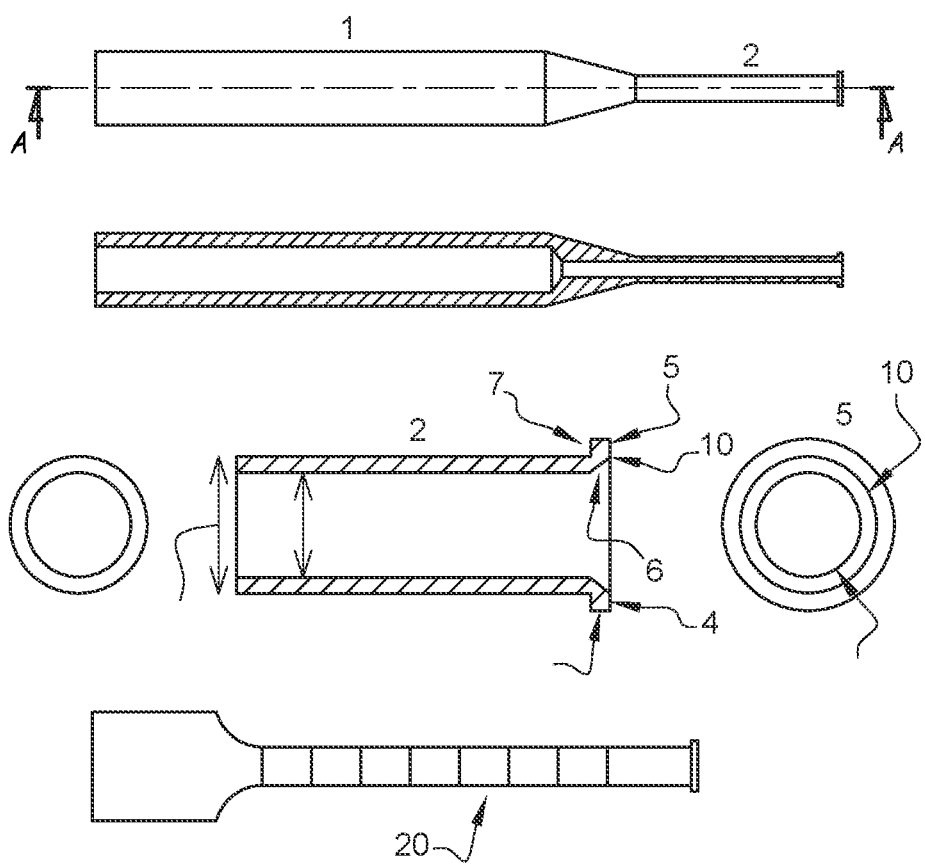
FIG. 7 shows exemplary views of a tool according to various embodiments of the disclosed technology.

Referring to FIG. 7, the hybrid punch according to the disclosed technology can be a single piece that is made from the stainless steel. It can include two hollow tubular structures. The wider proximal tubular structure (T1) can have an outer diameter of approximately 2.34 mm, which makes it compatible to fit in most dental handpieces. In various embodiments, the wider proximal tubular structure can serve as a suction chamber and can be housed in a dental handpiece that provides suction. In various embodiments, the hybrid punch can be housed in a dental handpiece that does not provide suction, and suction can be provided separately from the handpiece.

The disclosed tool includes a narrower, distal hollow tubular structure (T2) with a central axis and an end structure 3. The end structure terminates distally with a substantially flat and annular/ring-like face 4 that extends substantially in a plane perpendicular to the central axis of the punch and having a sharp cutting edge 5 at the outer perimeter of the annular face 4. In various embodiments, the sharp cutting edge 5 can be substantially circular and continuous. In various embodiments, the sharp cutting edge 5 can be non-circular and can be jagged or toothed.

Figure 20:
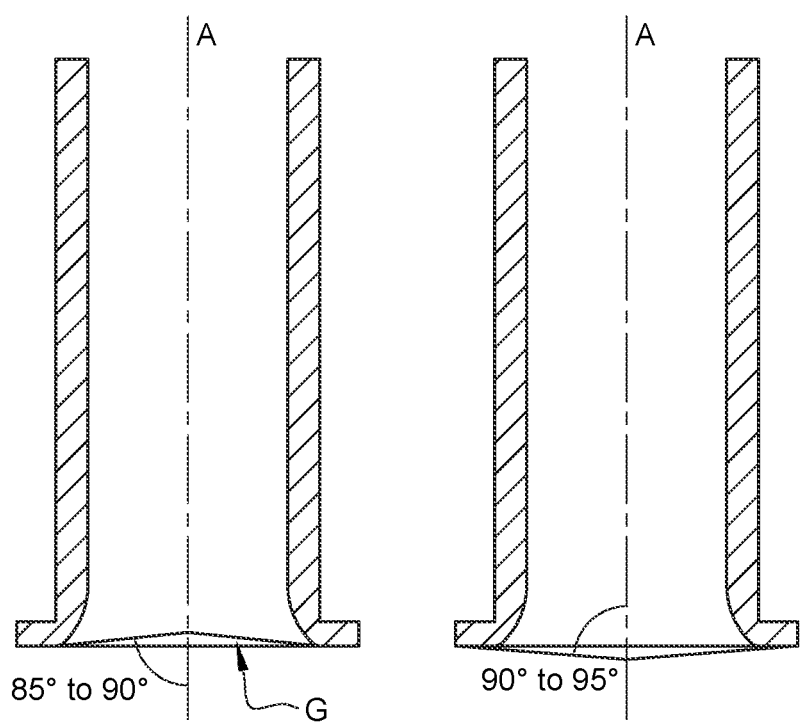
FIG. 20 shows an exemplary view of a cross-section of a tool, in accordance with aspects of the present disclosure.

Referring to FIGS. 7-18, a tool according to the disclosed technology has one or more of the following features. The tool includes a central axis, with the annular face 4 at the distal end of the tool. In various embodiments, each portion of the annular face 4 can be configured to be at an angle relative to the central axis that is between 80 to 100°, or that is between 85 to 95°, as shown in FIG. 20. In various embodiments, the angle can be between 87° to 93°. It is contemplated that, in various embodiments, the annular face 4 can form any angle in these disclosed ranges relative to the central axis. In various embodiments, the annular face 4 can be perpendicular to the central axis, as shown in FIG. 7.

With continuing reference to FIG. 7, in various embodiments, the annular or ring-like face 4 has a wall thickness between 50 μm and 100 μm, which is the difference between ExTr and IntTr. In various embodiments, the hollow tubular structure T2 has an external diameter ExDi between 0.7 mm and 1.4 mm and has a wall thickness between 50 and 150 μm. In various embodiments, the external diameter ExTr at the end of the end structure is greater than the outer diameter ExDi of the hollow tubular structure T2 by approximately 50 to 150 μm. In various embodiments, the external diameter ExTr at the end of the end structure is greater than the outer diameter ExDi of the hollow tubular structure T2 by no more than 200 μm.

In various embodiments, the inner edge 10 (InTr) of the flat annular face 4 of the end structure is substantially aligned with the outer surface of the hollow tubular structure T2 with diameter ExDi. Accordingly, the inner edge 10 of the flat annular face 4 of the end structure IntTr therefore has a diameter equal to or close to the diameter ExDi.

In various embodiments, the end structure 3 has a length of less than 1000 μm. In various embodiments, the end structure 3 has a length between 500 and 300 μm.

With continuing reference to FIG. 7, the end structure 3 has a smoothly curved inner surface 6 that smoothly connects to the inner surface of the hollow tubular structure T2. In various embodiments, the inner surface 6 of the end structure 3 is substantially in the shape of a half catenoid and forms part of a follicle receiving chamber.

In various embodiments, the outer edge 5 of the annular face 4 of the end structure is a sharp cutting edge. In various embodiments, the annular face 4 can be beveled to enhance the sharpness of the outer edge, as shown in FIG. 20. The inner edge 10 of the annular face 4 of the end structure is a non-cutting edge and can have a less abrupt angle or can be rounded.

Figure 21:
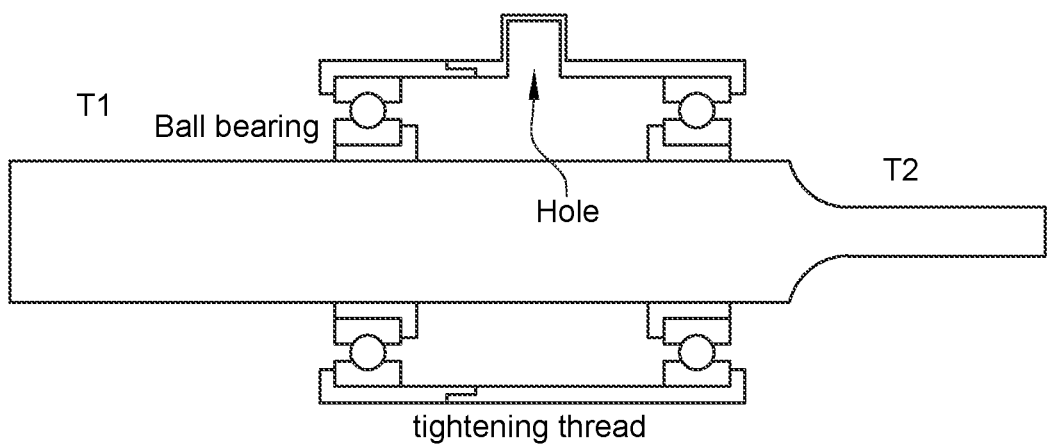
FIG. 21 shows an example of a suction system external to the punch, in accordance with aspects of the disclosed technology.

FIGS. 8-18 show diagrams of various embodiments of the end structures. As described below, the tools of FIGS. 8-18 include a tubular structure and an end structure that is wider than the tubular structure. The tools can be a single piece that is made from stainless steel and that has end portions as illustrated in any of FIGS. 8-18. The single piece can include two hollow tubular structures, as shown, for example, in FIG. 7. The wider proximal tubular structure (T1) can have an outer diameter of approximately 2.34 mm, which makes it compatible to fit in most dental handpieces. In various embodiments, the wider proximal tubular structure can serve as a suction chamber and can be housed in a dental handpiece that provides suction, as shown in FIG. 21. The tool includes a narrower, distal hollow tubular structure (T2) with a central axis and an end structure as shown in any of FIGS. 8-18.

The end structures of FIGS. 8-18 terminate distally with a substantially flat and annular/ring-like face that, in various embodiments, extends substantially in a plane perpendicular to the central axis of the punch and that has an outer edge. In various embodiments, each portion of the substantially annular face at the distal end of the tool can be configured to be at an angle relative to the central axis that is between 80 to 100°, or between 85 to 95°, as shown in FIG. 20. In various embodiments, the angle can be between 87° to 93°. In various embodiments, the flat annular face can be perpendicular to the central axis.

Figure 8:
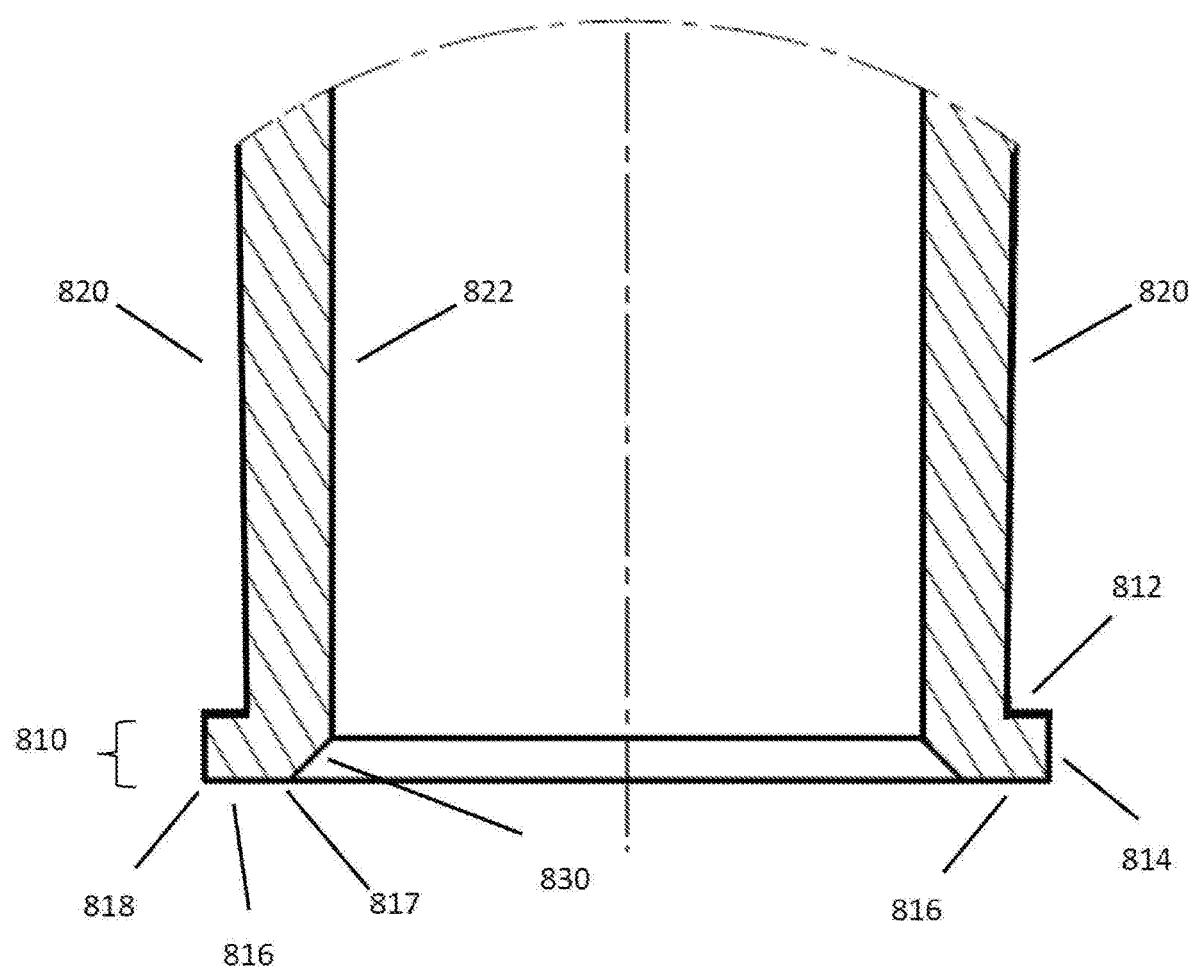
FIG. 8 shows exemplary views of a tool according to another embodiment of the disclosed technology.
Figure 10:
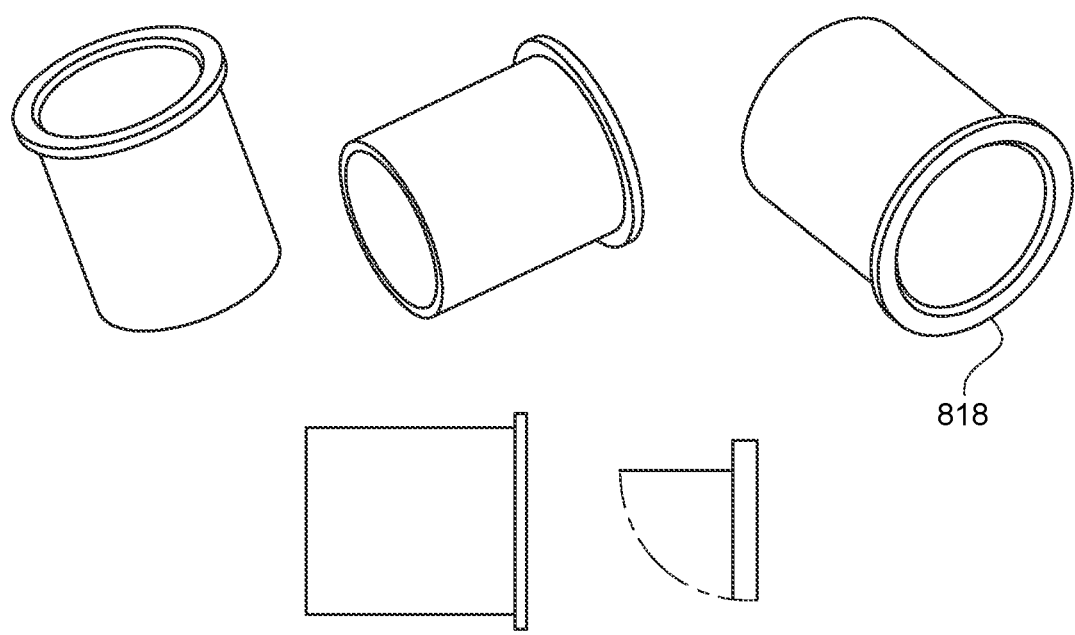
FIG. 10 shows perspective views of the tool of FIG. 8.
Figure 11:
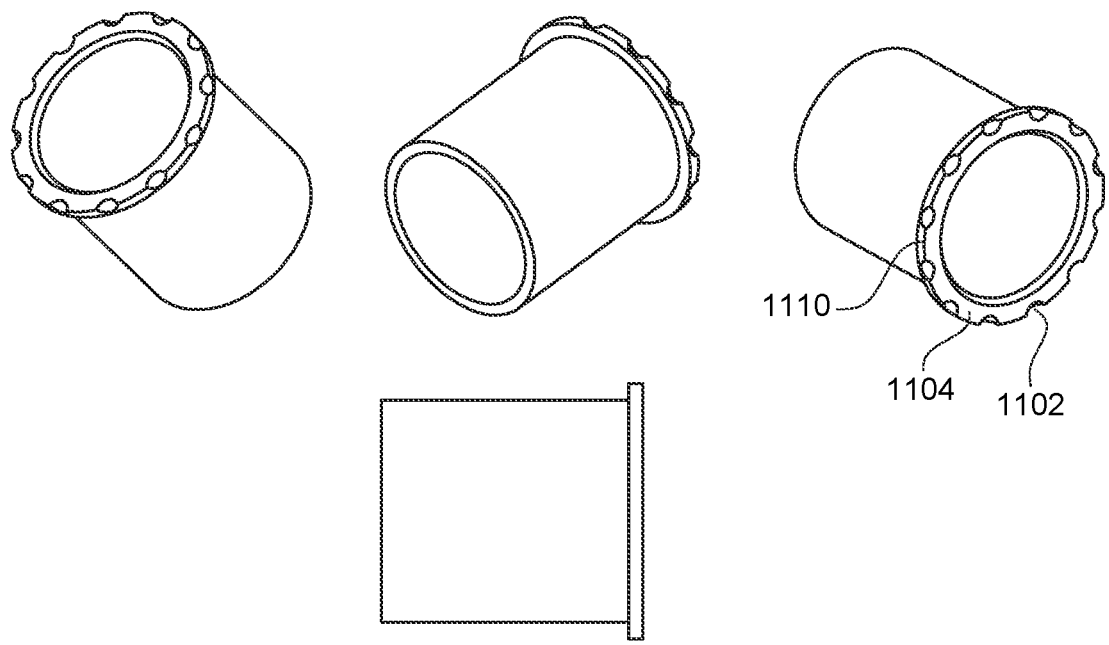
FIG. 11 shows exemplary views of the tool of FIG. 8 with notches and teeth, in accordance with aspects of the present disclosure.

Referring to FIG. 8, the end structure is in the shape of an annular ledge 810 having a top surface 812, a side surface 814, and a bottom surface that forms the flat annular face 816 described above. The top surface 812 can form a 90° angle or substantially a 90° angle with respect to the outer surface 820 of the tubular structure. In various embodiments, the top surface 812 can form another angle with respect to the outer 820 surface of the tubular structure. The top surface 812 of the annular ledge 810 can extend outward from the tubular structure by various widths. For example, in various embodiments, the top surface 812 can have a width between 50 and 100 μm. The side surface 814 connects the top surface 812 and the flat annular face 816 of the end structure. In various embodiments, the side surface 814 forms a straight connection or substantially a straight connection between the outer edge of the top surface 812 and the outer edge 818 of the flat annular face 816, as shown in FIG. 8. That is, the cross section of the end structure 810 does not include any curvature along the side surface 814 of the end structure. In various embodiments, the side surface 814 is parallel or substantially parallel to the central axis of the tubular structure. In various embodiments, the side surface 814 is perpendicular or substantially perpendicular to the flat annular face 816 of the end structure. In various embodiments, the inner edge 817 of the flat annular face 816 of the end structure can be substantially aligned between the inner wall 822 and outer wall 820 of the hollow tubular structure. The end structure includes an inner surface 830 that connects the inner edge 817 of the flat annular face with the inner wall 822 of the tubular structure. In various embodiments, the inner surface 830 cross section can form a straight line or substantially a straight line, as shown in FIG. 8. In various embodiments, the inner surface cross section can include a curvature and/or can smoothly connect the inner edge 817 of the flat annular face with the inner wall 822 of the tubular structure, such as a funnel shape shown in FIG. 5. A follicle receiving chamber extends proximally from the inner edge 817 of the flat annular face 816. In various embodiments, the outer edge 818 of the flat annular face can be substantially circular and continuous, as shown in FIG. 10. In various embodiments, the outer edge 818 can be non-circular and can be discontinuous and toothed, as shown in FIG. 11.

Figure 9:
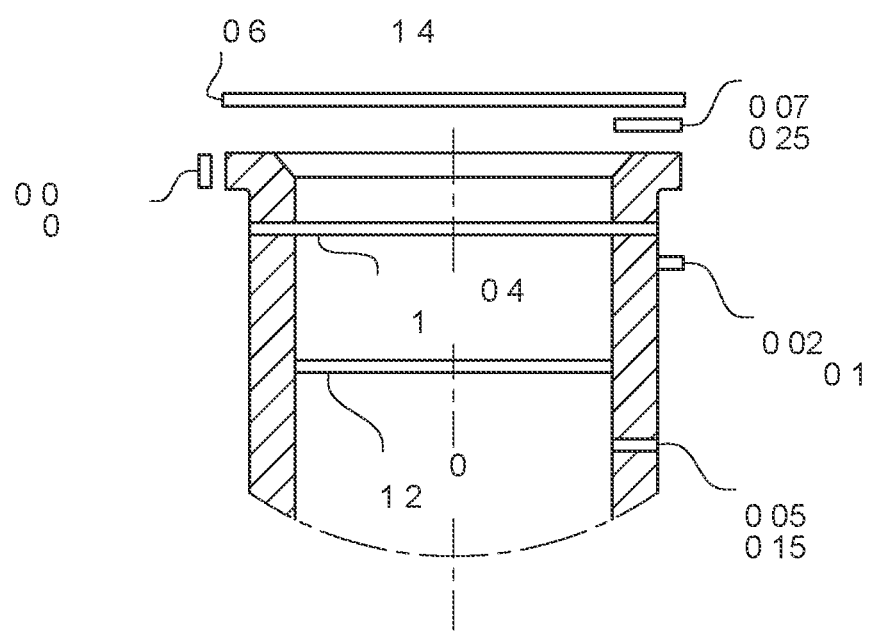
FIG. 9 shows exemplary dimensions of the tool of FIG. 8.

FIG. 9 shows various dimensions of various embodiments of the end structure of FIG. 8. The tubular structure can have outer dimensions between 0.4 mm and 1.3 mm, inner dimensions between 0.3 mm and 1.2 mm, and wall thickness between 0.05 mm and 0.15 mm. The end structure can be wider than the tubular structure and have outer dimensions between 0.6 mm and 1.4 mm. The annular ledge can have a top surface dimension between 0.02 mm and 0.1 mm and a side surface dimension between 0.03 mm and 3 mm. The dimension from the inner wall of the tubular structure to the outermost edge of the end structure can be between 0.07 mm and 0.25 mm.

Figure 12:
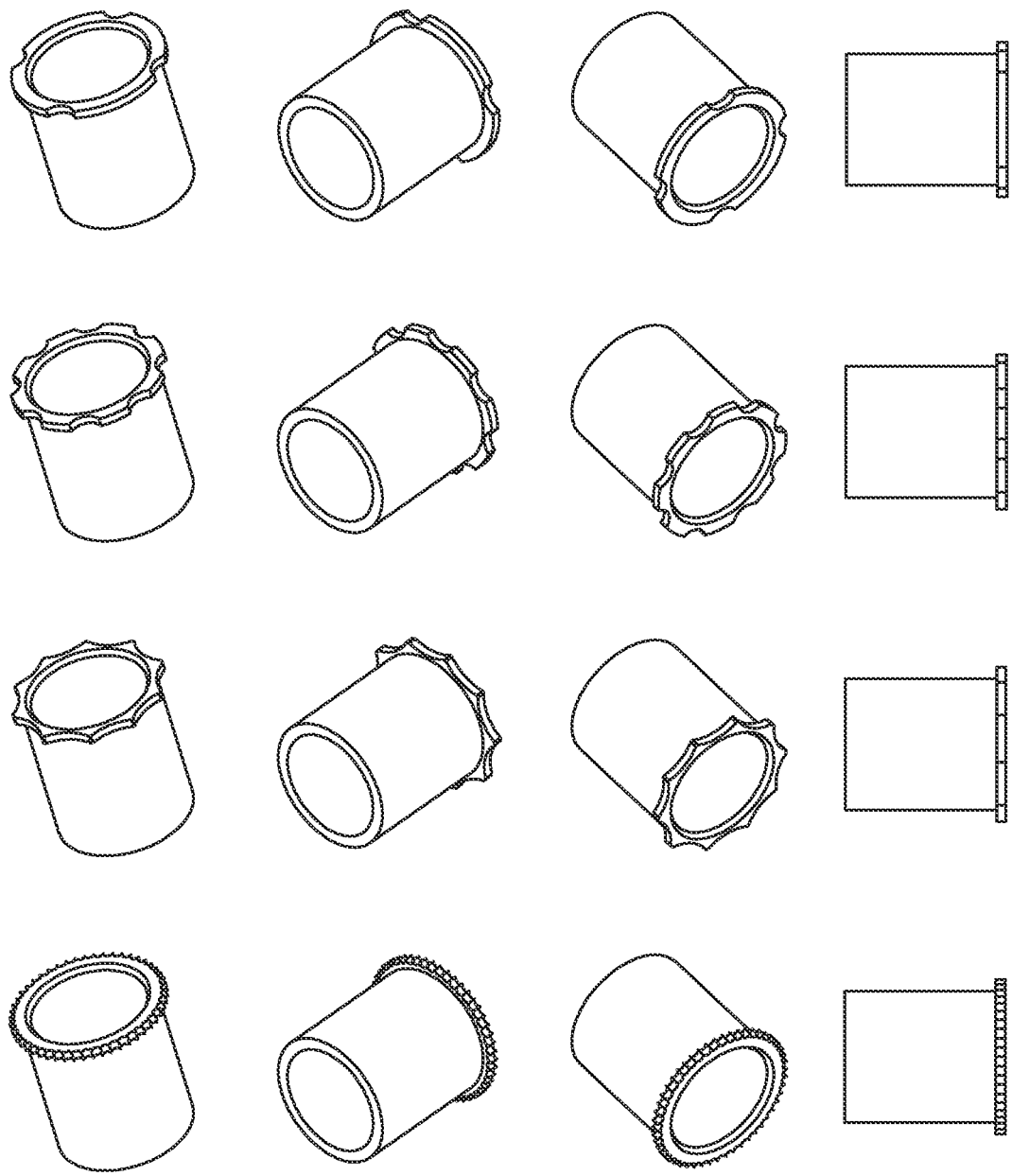
FIG. 12 shows exemplary views of the tool of FIG. 8 with different dimensions and numbers of notches and teeth, in accordance with aspects of the present disclosure.

FIG. 10 shows various perspectives of a punch having the end structure of FIG. 8, including various perspectives of the top surface, the side surface, the flat annular face, and other portions of the punch. In the illustrated embodiment, the cutting edge 818 (the outermost edge) is continuous). FIG. 11 shows various perspectives of a punch having the end structure of FIG. 8 with notches 1102 formed in the side surface and in the flat annular face of the annular ledge, but not in the top surface of the annular ledge. The notches 1102 form teeth 1104 at the flat annular face, such that the cutting edge 1110 (the outermost edge) of the flat annular face is toothed and discontinuous. FIG. 12 shows various perspectives of a punch having the end structure of FIG. 8 with notches formed in the side surface, the flat annular face, and the top surface of the annular ledge. The notches form teeth at the flat annular face, such that the cutting edge (the outermost edge) of the flat annular face is toothed and discontinuous. As shown in FIG. 12, the notches can vary in dimension and can provide different tooth shapes and different numbers of teeth, such as between 20 to 100 teeth. The illustrated embodiments are exemplary, and other variations are contemplated to be within the scope of the present disclosure.

Figure 13:
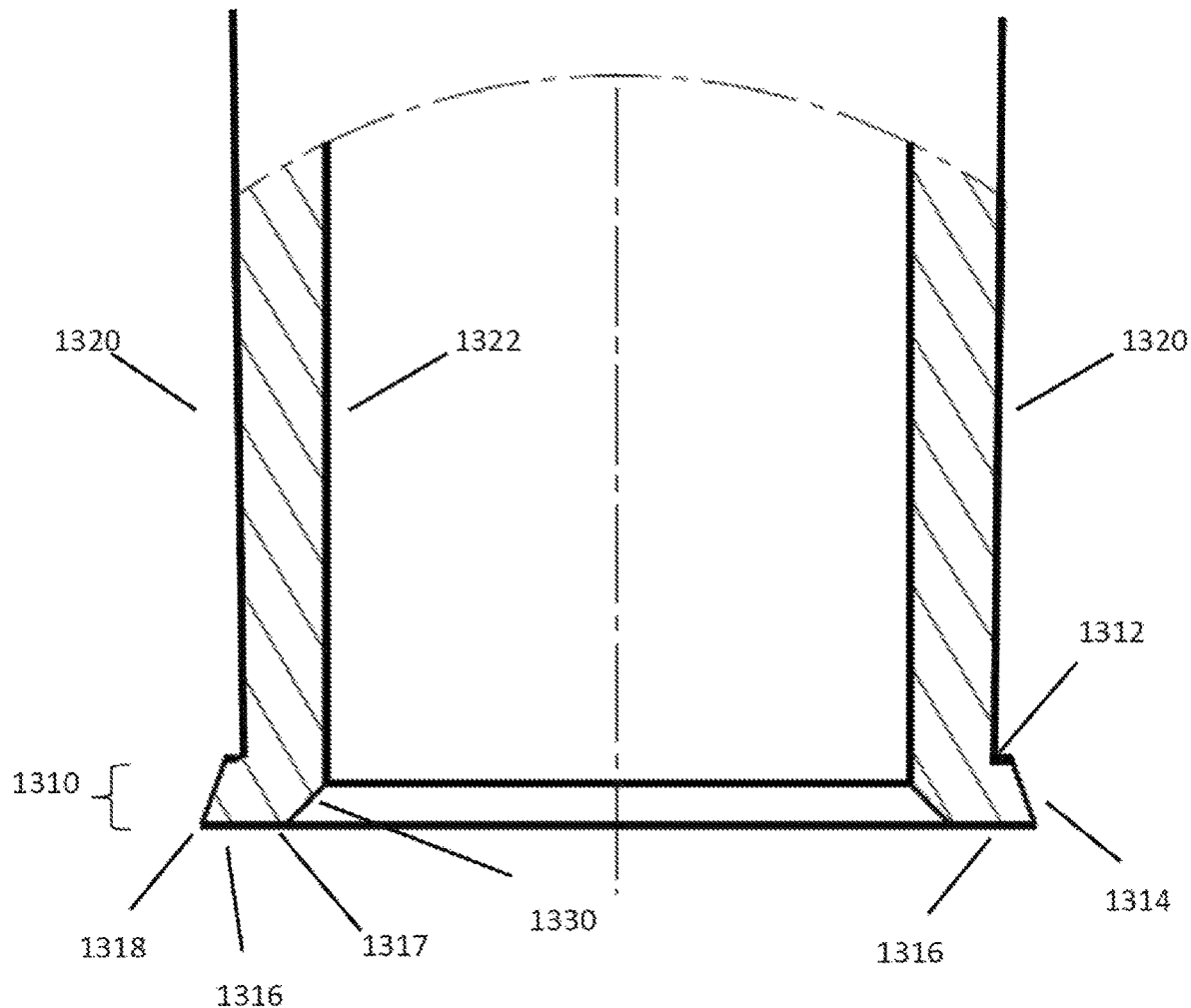
FIG. 13 shows an exemplary view of a tool according to another embodiment of the disclosed technology.
Figure 14:
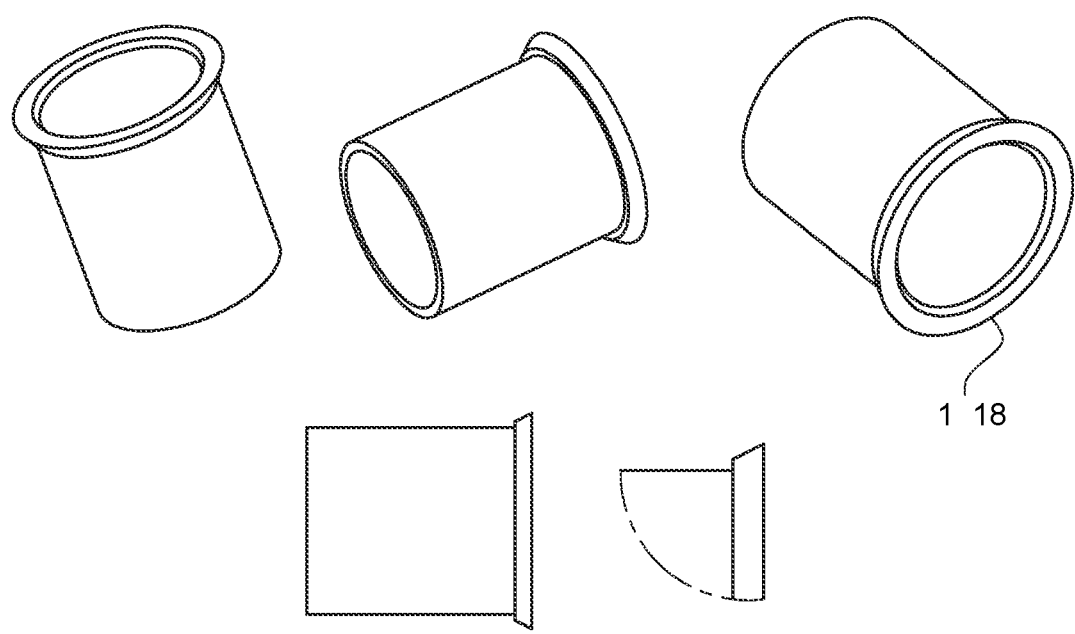
FIG. 14 shows perspective views of the tool of FIG. 13.
Figure 15:
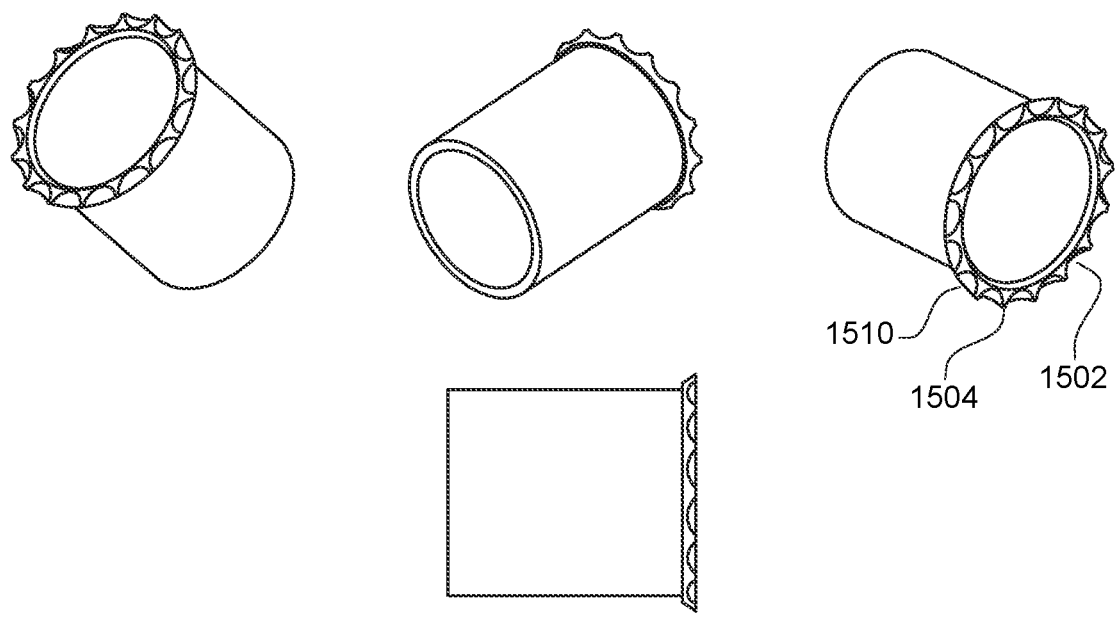
FIG. 15 shows exemplary views of the tool of FIG. 13 with notches and teeth, in accordance with aspects of the present disclosure.

Referring to FIG. 13, another end structure is in the shape of an annular ledge 1310 having a top surface 1312, a beveled side surface 1314, and a bottom surface that forms the flat annular face 1316 described above. The top surface 1312 can form a 90° angle or substantially a 90° angle with respect to the outer surface 1320 of the tubular structure. In various embodiments, the top surface 1312 can form another angle with respect to the outer surface 1320 of the tubular structure. The top surface 1312 of the annular ledge can extend outward from the tubular structure by various widths. For example, in various embodiments, the top surface 1312 can have a width between 10 and 50 μm. The beveled side surface 1314 connects the top surface 1312 and the flat annular face 1316 of the end structure. In various embodiments, the beveled side surface 1314 forms a straight connection or substantially a straight connection between the outer edge of the top surface 1312 and the outer edge 1318 of the flat annular face, as shown in FIG. 13. That is, the cross section of the end structure does not include any curvature along the side surface 1314 of the end structure. In various embodiments, the side surface 1314 of the annular ledge forms a sharp edge 1318 with the flat annular face 1316. The angle between the side surface 1314 and the flat annular face 1316 is less than 90°. In various embodiments, the annular face can be beveled to enhance the sharpness of the outer edge, as shown in FIG. 20. In various embodiments, the inner edge 1317 of the flat annular face of the end structure can be substantially aligned between the inner wall 1322 and outer wall 1320 of the hollow tubular structure. The end structure includes an inner surface 1330 that connects the inner edge 1317 of the flat annular face with the inner wall 1322 of the tubular structure. In various embodiments, the inner surface 1330 cross section can form a straight line or substantially a straight line, as shown in FIG. 13. In various embodiments, the inner surface 1330 cross section can include a curvature and/or can smoothly connect the inner edge 1317 of the flat annular face with the inner wall 1322 of the tubular structure, such as a funnel shape shown in FIG. 5. A follicle receiving chamber extends proximally from the inner edge 1317 of the flat annular face. In various embodiments, the outer edge 1318 of the flat annular face can be substantially circular and continuous, as shown in FIG. 14. In various embodiments, the outer edge can be non-circular and can be jagged or toothed, as shown in FIG. 15. Also, various of the dimensions described above and/or in FIG. 7 and/or FIG. 9 are applicable to the embodiment of FIG. 13.

FIG. 14 shows various perspectives of a punch having the end structure of FIG. 13, including various perspectives of the top surface, the beveled side surface, the flat annular face, and other portions of the punch. In the illustrated embodiment, the cutting edge 1318 (the outermost edge) is continuous. FIG. 15 shows various perspectives of a punch having the end structure of FIG. 13 with notches 1502 formed in the beveled side surface and the flat annular face of the annular ledge, but not in the top surface of the annular ledge. The notches 1502 form teeth 1504 at the flat annular face, such that the cutting edge 1510 (the outermost edge) of the flat annular face is toothed and discontinuous. The illustrated embodiments are exemplary and variations are contemplated to be within the scope of the present disclosure. For example, the notches and teeth can have different dimensions than as illustrated and there can be different numbers of teeth, such as between 20 to 100 teeth. In various embodiments, the notches can reach the top surface of the annular ledge as well.

Figure 16:
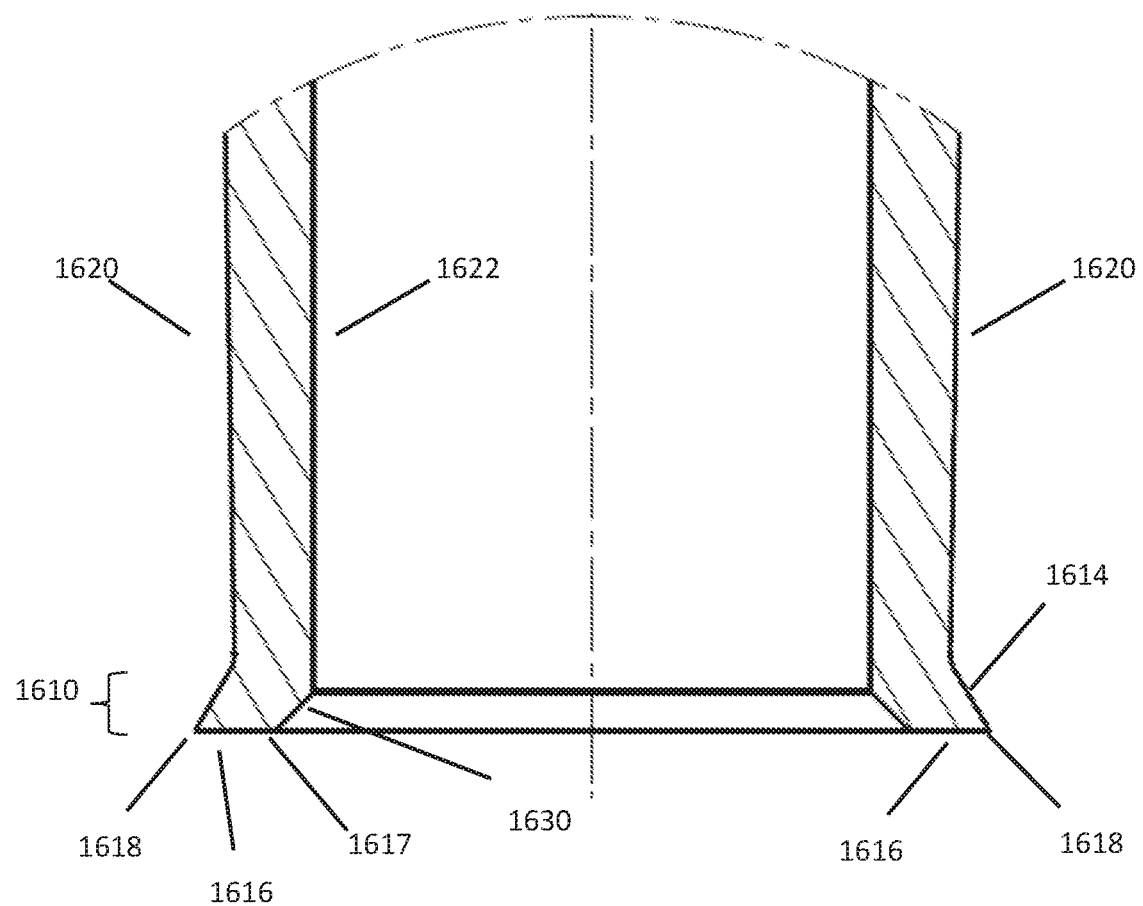
FIG. 16 shows an exemplary view of a tool according to another embodiment of the disclosed technology.
Figure 17:
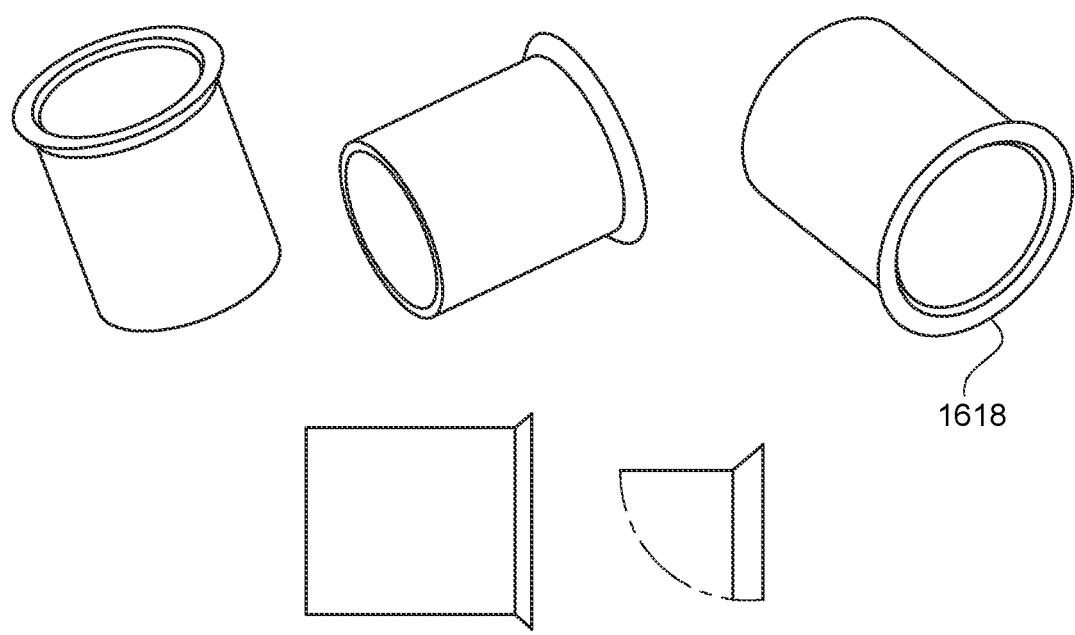
FIG. 17 shows perspective views of the tool of FIG. 16.
Figure 18:
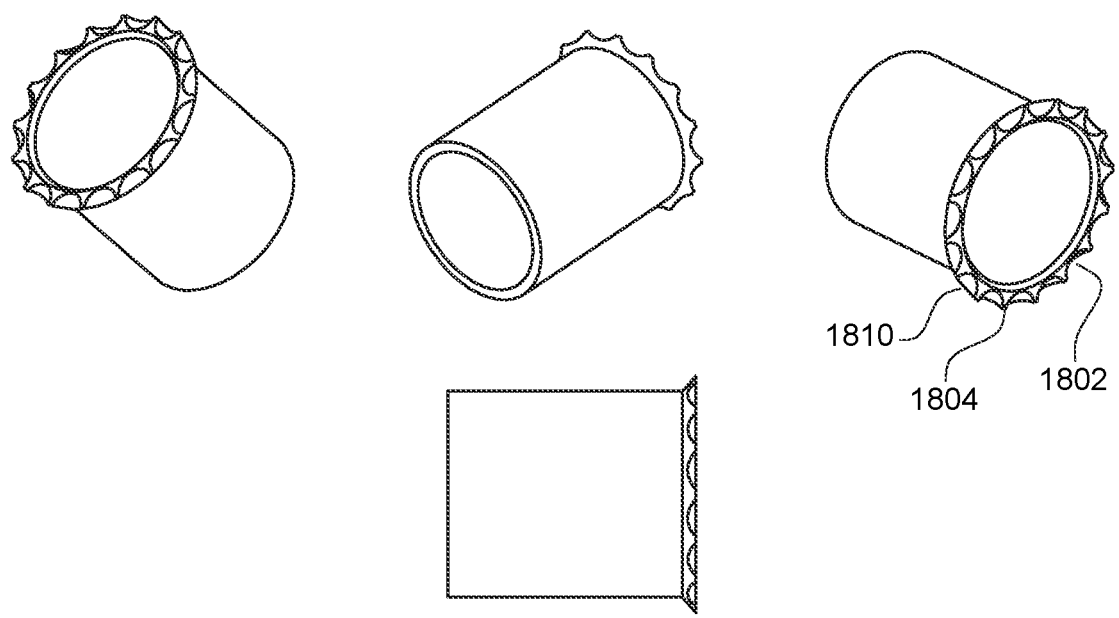
FIG. 18 shows exemplary views of the tool of FIG. 16 with notches and teeth, in accordance with aspects of the present disclosure.

Referring to FIG. 16, the end structure is in the shape of a structural skirt 1610 having an inclined surface 1614 and a bottom surface that forms the flat annular face 1616 described above. The inclined surface 1614 connects the tubular structure and the flat annular face 1616 of the end structure. In various embodiments, the inclined surface 1614 forms a straight connection or substantially a straight connection between the outer wall 1620 of the tubular structure and the outer edge 1618 of the flat annular face, as shown in FIG. 16. That is, the cross section of the end structure does not include any curvature along the inclined surface 1614 of the end structure. The inclined surface 1614 forms a sharp edge 1618 with the flat annular face 1616. In various embodiments, the annular face can be beveled to enhance the sharpness of the outer edge, as shown in FIG. 20. In various embodiments, the inner edge 1617 of the flat annular face of the end structure can be substantially aligned between the inner wall 1622 and outer wall 1620 of the hollow tubular structure. The end structure includes an inner surface 1630 that connects the inner edge 1617 of the flat annular face with the inner wall 1622 of the tubular structure. In various embodiments, the inner surface 1630 cross section can form a straight line or substantially a straight line, as shown in FIG. 16. In various embodiments, the inner surface 1630 can include a curvature and/or can smoothly connect the inner edge 1617 of the flat annular face with the inner wall 1622 of the tubular structure, such as a funnel shape shown in FIG. 5. A follicle receiving chamber extends proximally from the inner edge 1617 of the flat annular face 1616. In various embodiments, the outer edge 1618 of the flat annular face 1616 can be substantially circular and continuous, as shown in FIG. 17. In various embodiments, the outer edge can be non-circular and can be jagged or toothed, as shown in FIG. 18. Also, various of the dimensions described above and/or in FIG. 7 and/or FIG. 9 are applicable to the embodiment of FIG. 16.

FIG. 17 shows various perspectives of a punch having the end structure of FIG. 16, including various perspectives of the inclined surface and the flat annular face, and other portions of the punch. In the illustrated embodiment, the cutting edge 1618 (the outermost edge) is continuous. FIG. 18 shows various perspectives of a punch having the end structure of FIG. 16 with notches 1802 formed in the inclined surface and the flat annular face of the structural skirt. The notches 1802 form teeth 1804 at the flat annular face, such that the cutting edge 1810 (the outermost edge) of the flat annular face is toothed and discontinuous. The illustrated embodiments are exemplary and variations are contemplated to be within the scope of the present disclosure. For example, the notches and teeth can have different dimensions than as illustrated and there can be different numbers of teeth, such as between 20 to 100 teeth.

Figure 19:
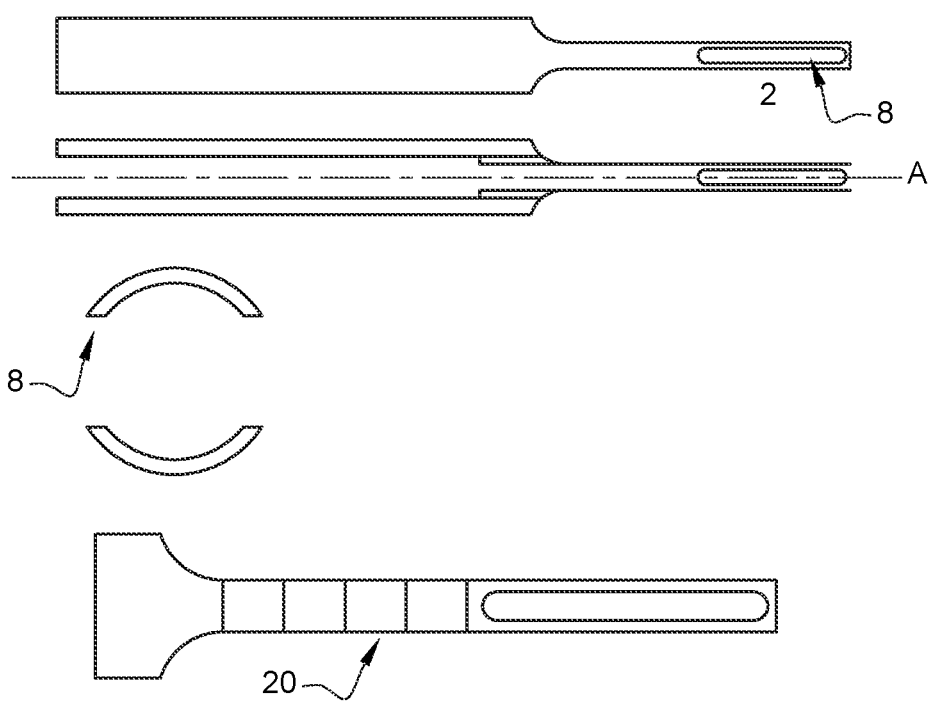
FIG. 19 shows exemplary views of a tool according to another aspect of the disclosed technology, in which windows are provided in the tool.

Referring now to FIG. 19, the hollow tubular structure may have one or more windows 8 that provide a view of the hair to be harvested within the hollow tubular structure. In the illustrated embodiment of FIG. 19, two windows 8 opposite each other and positioned 180 degrees apart are arranged on the lower part 2 of the hollow tubular structure just above the end structure.

The windows of FIG. 19 provide two advantages. As mentioned above, the windows allow a view of the hair and thus allow a user to accurately position the punch around the hairs. Secondly, friction between the hairs and the punch is reduced due to decreased inner surface area because of the windows, thereby allowing the punch to be driven deeper into the dermis while avoiding a phenomenon known as the "missing graft" (graft failure). A missing graft can occur when a conventional punch is inserted too deeply and causes twisting of the follicle, which can lead to a shortening of the latter and to "suction" inside the skin. The graft can disappear to completely from the operating field, and it is virtually impossible to recover it. The windows of FIG. 19 can apply to any of the embodiments described above herein.

Referring now to FIG. 21, the disclosed technology can include a suction chamber T1 attached to the hollow tubular structure T2. This suction chamber can be connected to a pump (not shown). When the punch is housed in a handpiece, the pump can be located away from the handpiece or attached to the handpiece. This suction can aspirate the blood that pools in the holes made in the skin. This also allows lightly suctioning the follicle during extraction and securing it by preventing it from rotating inside the punch. The suction chamber of FIG. 21 can apply to any of the embodiments disclosed above herein.

Referring to FIGS. 7 and 19, in one aspect of the disclosed technology, size indicators such as line or circular markings can, be affixed to the outer surface of the wider tubular structure T1 to indicate the size of the punch to the operator. Such size can correspond to the outer diameter of the flat annular face of the end structure (ExTr). It, therefore, corresponds to the actual size of the hole created by the distal part of the narrower tubular structure (T2). In accordance with the disclosed technology, the hybrid punches can have the following sizes: size 1: 0.7 mm; size 2: 0.75 mm; size 3: 0.8 mm; size 4: 0.85 mm; size 5: 0.9 mm; size 6: 0.95 mm; size 7: 1 mm; size 8: 1.05 mm; size 9: 1.1 mm; size 11: 1.2 mm. Other sizes not expressly stated herein are contemplated and are encompassed by the disclosed technology.

In one aspect of the disclosed technology, the thickness of the tubular structure wall is adapted to its diameter. In various embodiments, the wall thickness can range from 0.08 mm (80 µm) and 0.12 mm (120 µm).

For example, a punch of 0.9 mm will have an external diameter of 0.9 mm for face of the end structure. Correspondingly, the hollow tubular structure T2 will have an inner diameter of 0.75 mm and an outer diameter of 0.9 mm.

In one aspect of the disclosed technology, and referring to FIGS. 7 and 19, the tubular structure T2 can include depth indicators 20, such as graduated markings, that indicate the depth at which the punch is located below the surface of the skin. In various embodiments, a marking can be placed every 500 µm along the outer surface of the tubular structure T2.

Referring to FIG. 19, the windows 8 can be positioned just above the end structure and the size of the windows can depend on the size of the tubular structure T2. For example, the size of the windows 8 can increase with the diameter of the tubular structure T2. For example a punch of size 0.9 mm can have two windows of size 3 mm by 0.6 mm.

Figure 22:
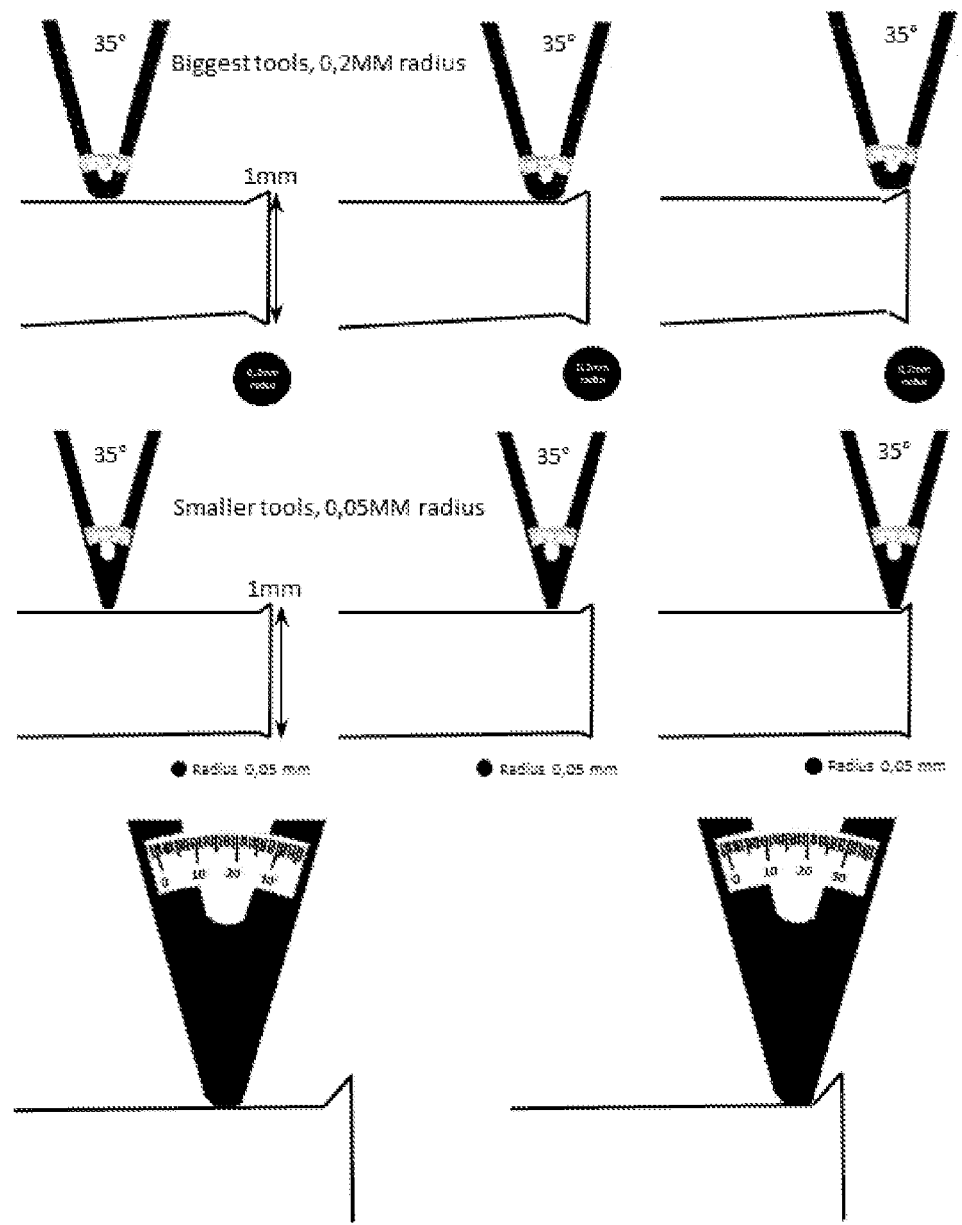
FIG. 22 shows exemplary views of different manufacturing tool configurations for shaping the end structure of a tool, in accordance with aspects of the disclosed technology.

FIG. 22 shows exemplary views of different manufacturing tool configurations for shaping the end structure of the tool of FIG. 16. In various embodiments, the end portion of the punch tool can initially be manufactured with a lump or block of material, such as stainless steel or another material. The shaping tool can be used to remove portions of the lump or block of material to shape it into the end structures disclosed herein, such as the end structures shown in FIGS. 8, 13, and 16.

In the illustrated embodiments, the shaping tool has a rounded end portion that contacts the punch material to remove material, and has an angled portion that extends from the rounded end portion. As shown in FIG. 22, the shaping tool can have different sizes for the rounded end portion, including rounded end portion having a 0.2 mm radius or having a 0.05 mm radius. The angled portion can form different angles. In FIG. 22, the angle of the angled portion is 35 degrees, but can be another angle. The size of the rounded end portion and the angle of the angled portion of the shaping tool may affect the ultimate shape of the end structure and/or the shape of the junction between the tubular structure and the end structure of the punch. For example, as shown in FIG. 22, if the size of the rounded end portion of the shaping tool is larger, it may be more difficult to achieve an abrupt angle at the junction between the tubular structure and the end structure of the punch. If the size of the rounded end portion of the shaping tool is smaller, it may be easier to achieve an abrupt angle at the junction between the tubular structure and the end structure of the punch.

In accordance with aspects of the present disclosure, for any of the punch configurations disclosed herein, the junction between the tubular structure and the end structure of the punch may be an abrupt angle or may be a gradual transition, such as an arc. As long as aspects of the disclosed punches are present, such junctions are contemplated to be within the scope of the present disclosure.

Figure 23:
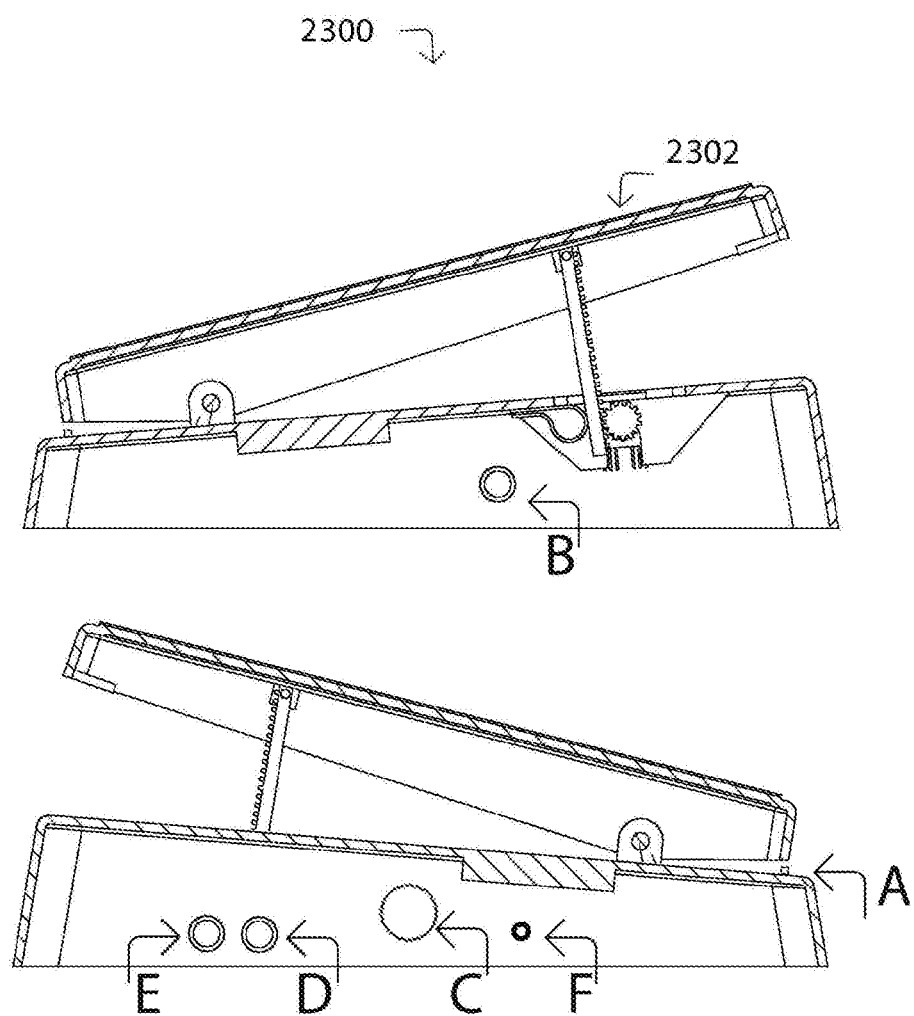
FIG. 23 shows examples of a pedal equipped with various control buttons, in accordance with aspects of the disclosed technology.
Figure 24:
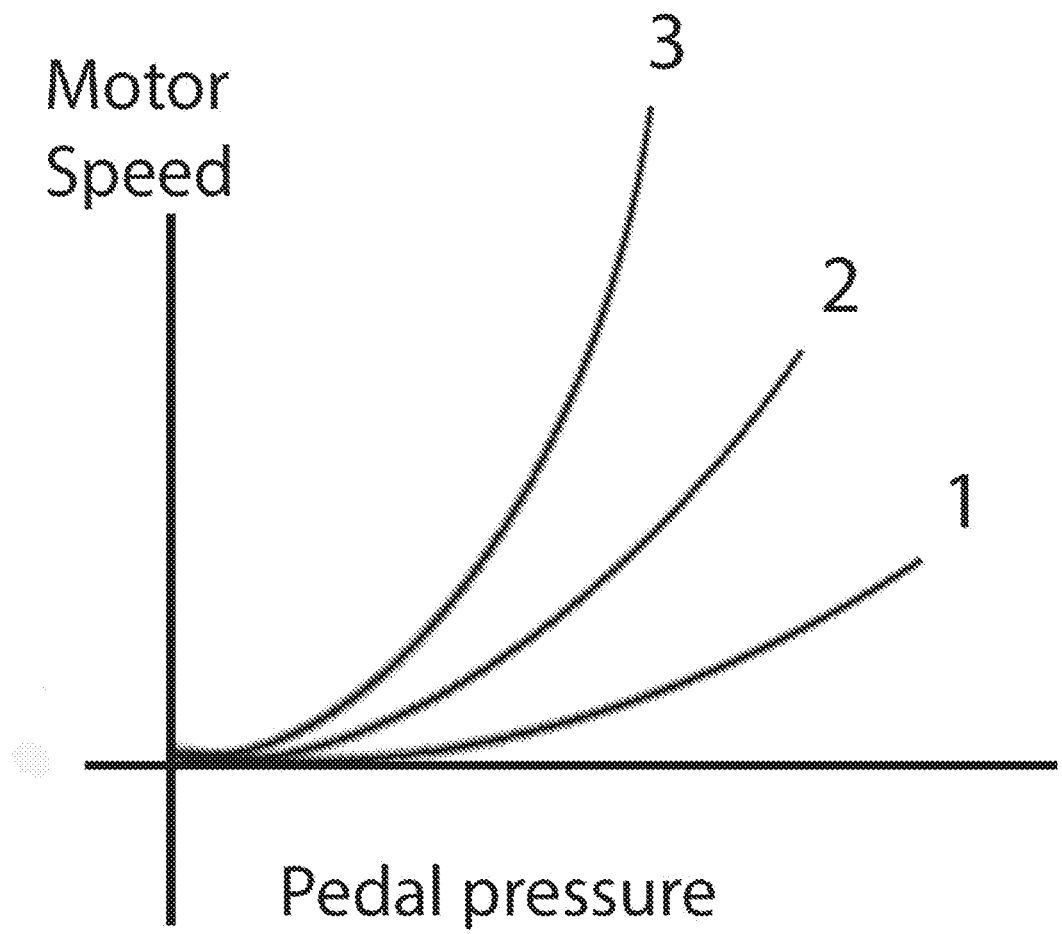
FIG. 24 shows examples of correlation between pedal pressure and motor speed, in accordance with different embodiments of the disclosed technology.

What will now be described in connection with FIGS. 23 and 24 are parts of the disclosed tool motorizing the disclosed punch. FIG. 23 is an illustration of a foot pedal 2300 in accordance with various embodiments of the disclosed technology. The pedal includes a top plate 2302 which pivots and can travel a distance of, for example, 5 cm. The pedal can control rotation/oscillation of the disclosed punch through a motor (not shown), and the depression of the pedal top plate 2302 enables the rotational/oscillatory speed of the punch to be varied with precision. Outlet B provides a port or jack or connection through which the foot pedal can communicate with and power the motor for rotating/oscillating the disclosed punch. In another embodiment, the foot pedal can communicate wirelessly with the motor, such as by Bluetooth or another wireless protocol, and the motor can have a separate power source.

In various embodiments, the pedal 2300 can include various knobs or buttons or interfaces, each having different functions, as described in the following disclosure.

In various embodiments the foot pedal 2300 can be powered by a battery (not shown). The first button A, located below the pedal, allows powering of the motor only when the pedal is actively used. In other words, button A serves to prevent powering of the motor when the pedal is not actively used. In this way, the battery is very slightly discharged when the foot pedal 2300 is not actively used. In this manner, the batteries can operate for extended periods without recharging. In various embodiments, the battery can provide power for 72 hours without recharging.

In the illustrated embodiment, the foot pedal 2300 can provide an indication that the battery will be imminently discharged, which provides a degree of protection against the complete discharge or depletion of the batteries. In various embodiments, a red flashing button (not shown) can warn of impending discharge or depletion of the battery and can notify a user to charge the batteries. In various embodiments, the batteries can be recharged with a charger (not shown) that plugs into the socket F. The plug can be compatible with all regions of the world.

In the illustrated embodiment, button C enables the very precise modification of the amount of angular rotation of the punch. In various embodiments, the disclosed punch can rotate around its axis alternating successively between clockwise rotation and counter-clockwise rotation. In various embodiments, each clockwise rotation or counter-clockwise rotation can be between 30° and 360°, and button C is used to adjust the number of degrees of this angular rotation in each direction. In some embodiments, the angular rotation can be more than 360°.

In one aspect of the disclosed technology, the rotation/oscillation speed or angular velocity of the punch can be controlled. With reference also to FIG. 24, the illustrated graph shows that displacement of the foot pedal can increase the angular velocity of the punch rotation exponentially depending on the intensity of the thrust on the pedal. The foot pedal can include different correlations between pedal pressure and the motor driving the rotation/oscillation of the punch, as illustrated. Knob D, illustrated in FIG. 23, can be used to modify the correlation or progression curve. In various embodiments, turning the knob D clockwise straightens the curve (for example, 1 towards 2 towards 3) which allows for greater responsiveness of the pedal.

In various embodiments, button E allows adjusting the level of the initial starting speed of the motor. It does not alter the progression of the motor speed as shown in FIG. 24 and is a separate functionality. Button E can be set at the first use and need not be set again unless a different motor is connected.

Accordingly, what has been described above herein is a pedal, activated by the operator's foot, which launches the rotation/oscillation of the punch and controls it in a precise manner. In use, the disclosed system can limit the movements of the punch when necessary. When piercing the epidermis as shown in FIG. 5 or FIG. 6, a speed between 60 and 300 clockwise-counter-clockwise rotations/oscillations per minute can be achieved with the disclosed system. Then, when the punch penetrates into the deep dermis, the rotational/oscillatory speed can be decreased further. The disclosed system also allows, via the adjusting knobs, to change the amount of angular rotation in order to minimize the twisting of the follicle, which results from friction between the graft and the inner part of the punch. The recommended amount of angular rotation in the clockwise direction and the counter-clockwise direction is between 30° and 360°, depending on the quality of the skin. It is common to successfully extract a graft with a succession of about a dozen clockwise and counter-clockwise rotations/oscillations.

The disclosed pedal can include circuitry, processors, microcontrollers, programmable logic devices, ASICS, memory, software, firmware, and/or other software or hardware to perform the disclosed operations. The disclosed buttons and knobs on the pedal are exemplary and other interfaces are contemplated, such as switches, slides, and touch screens.

A punch in accordance with the disclosed technology is capable of extracting between 4000 and 8000 grafts before being replaced.

A punch according to the disclosed technology can be driven much deeper than a sharp punch of an equivalent diameter, with lesser risk of damage. This penetration depth may be equal to the length of a hair follicle, such as between 3 and 5 mm. The result is the ability to obtain high quality grafts, with very low transection rate and, at the same time, a higher number of hairs per graft (follicular density) than with a sharp punch of the same diameter. Additionally, the actual extraction step is facilitated because the attachments of the surrounding tissue are more deeply broken than with a sharp punch, which operates more superficially. The disclosed system operates significantly faster than prior systems. Even if the actual cutting step may, in some cases, be slightly slower than with "sharp" punches, the shortening of the extraction step shortens the total extraction operating time. With prior systems, an experienced practitioner can extract up to 600 grafts per hour when the extraction step is separated from the cutting step (that is to say, the cutting step carried out with the punch comes to a stop during the extraction step with another tool or part of a tool). In contrast, the tool according to the disclosed technology can permit hourly follicular extraction rates of around 1000 grafts per hour.

The use of the disclosed hybrid punches can be particularly effective in cases that are generally difficult to treat. These include extraction of old grafts that are too voluminous, of hair grafts in African patients, and of beard grafts.

In the first case, the hair is often spaced further apart from each other than in a conventional situation. Furthermore, the internal micro-scars increase the strength of the attachment of the hair to the surrounding tissue. Among African patients, the hairs are highly curved in the shape of commas and their extraction is often extremely difficult, if not impossible, with the conventional technique of sharp punches. Finally, as to beard hairs, the hairs extracted almost never have lesions.

Those skilled in the art will recognize that the disclosed embodiments are illustrative and do not limit the scope of the disclosed technology. It is contemplated that various embodiments can be combined. The scope of the disclosed technology will be defined by the claims, which are appended hereto.

What is claimed is:

1. An apparatus for harvesting hair follicles from a skin donor site by rotating or oscillating motion, the apparatus comprising:
   a hollow tubular structure having a central axis and an outer wall presenting a first external diameter;
   an annular ledge attached to an end of the hollow tubular structure, the annular ledge presenting a second external diameter larger than the first external diameter and terminating distally at a substantially flat annular face that is substantially in a plane perpendicular to the central axis, the annular ledge including:
      a top surface extending radially outward from the outer wall of the hollow tubular structure,
      the substantially flat annular face having a non-cutting inner edge, and
      a side surface connecting the top surface and the substantially flat annular face and that is at least one of: substantially parallel to the central axis or substantially perpendicular to the substantially flat annular face, wherein a sharp cutting edge is formed by the connection of the side surface with the substantially flat annular face; and
   a follicle receiving chamber extending proximally from the non-cutting inner edge of the substantially flat annular face.

2. The apparatus of claim 1, wherein the top surface is substantially perpendicular to the hollow tubular structure.

3. The apparatus of claim 2, wherein a junction formed by the top surface of the annular ledge and the outer wall of the hollow tubular structure is discontinuous.

4. The apparatus of claim 1, wherein the follicle receiving chamber is smoothly varying.

5. The apparatus of claim 1, wherein the substantially flat annular face includes notches such that the sharp cutting edge is non-continuous.

6. The apparatus of claim 5, wherein the annular ledge includes teeth between the notches.

7. The apparatus of claim 1, wherein the substantially flat annular face forms an angle with the central axis that is between 80° to 100°.

8. An apparatus for harvesting hair follicles from a skin donor site by rotating or oscillating motion, the apparatus comprising:
   a hollow tubular structure having a central axis and an outer wall presenting a first external diameter;
   an annular ledge attached to an end of the hollow tubular structure, the annular ledge presenting a second external diameter larger than the first external diameter and terminating distally at a substantially flat annular face that is substantially in a plane perpendicular to the central axis, the annular ledge including:
      a top surface extending radially outward from the outer wall of the hollow tubular structure,
      the substantially flat annular face having a non-cutting inner edge, and
      a beveled side surface connecting the top surface and the substantially flat annular face, wherein a sharp cutting edge is formed by the connection of the beveled side surface with the substantially flat annular face; and
   a follicle receiving chamber extending proximally from the non-cutting inner edge of the substantially flat annular face.

9. The apparatus of claim 8, wherein the top surface is substantially perpendicular to the hollow tubular structure.

10. The apparatus of claim 9, wherein a junction formed by the top surface of the annular ledge and the outer wall of the hollow tubular structure is discontinuous.

11. The apparatus of claim 8, wherein the follicle receiving chamber is smoothly varying.

12. The apparatus of claim 8, wherein the substantially flat annular face includes notches such that the sharp cutting edge is non-continuous.

13. The apparatus of claim 12, wherein the annular ledge includes teeth between the notches.

14. The apparatus of claim 8, wherein the substantially flat annular face forms an angle with the central axis that is between 80° to 100°.

15. An apparatus for harvesting hair follicles from a skin donor site by rotating or oscillating motion, the apparatus comprising:
   a hollow tubular structure having a central axis and an outer wall presenting a first external diameter;
   a structural skirt attached to an end of the hollow tubular structure, the structural skirt presenting a second external diameter larger than the first external diameter and terminating distally at a substantially flat annular face that is substantially in a plane perpendicular to the central axis, the structural skirt including:
      the substantially flat annular face having a non-cutting inner edge, and
      an inclined surface connecting the hollow tubular structure and the substantially flat annular face, the inclined surface being inclined with respect to the outer wall of the hollow tubular structure, wherein a sharp cutting edge is formed by the connection of the inclined surface with the flat annular face; and
   a follicle receiving chamber extending proximally from the non-cutting inner edge of the substantially flat annular face.

16. The apparatus of claim 15, wherein a junction formed by the inclined surface of the structural skirt and the outer wall of the hollow tubular structure is discontinuous.

17. The apparatus of claim 15, wherein the follicle receiving chamber is smoothly varying.

18. The apparatus of claim 15, wherein the substantially flat annular face includes notches such that the sharp cutting edge is non-continuous.

19. The apparatus of claim 18, wherein the structural skirt includes teeth between the notches.

20. The apparatus of claim 15, wherein the substantially flat annular face forms an angle with the central axis that is between 80° to 100°.

* * * * *